United States Patent
Reddy et al.

(10) Patent No.: US 7,560,585 B2
(45) Date of Patent: Jul. 14, 2009

(54) PROCESS FOR PREPARING (S)-ALPHA-CYANO-3-PHENOXYBENZYL-(S)-2-(4-CHLOROPHENYL)-ISOVALERATE

(75) Inventors: Vaddu Venkata Narayana Reddy, Hyderabad (IN); Khwaja Ishratullah, Hyderabad (IN); Penumatcha Venkata Krishnam Raju, Hyderabad (IN); Tella Ramesh Babu, Hyderabad (IN); Masna Mahesh, Hyderabad (IN); Chappeta Venkateswara Reddy, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 475 days.

(21) Appl. No.: 11/009,946

(22) Filed: Dec. 10, 2004

(65) Prior Publication Data

US 2006/0128982 A1   Jun. 15, 2006

(51) Int. Cl.
*C07C 255/03* (2006.01)
(52) U.S. Cl. ..................... 558/441; 558/410
(58) Field of Classification Search .......... 558/441, 558/410
See application file for complete search history.

(56) References Cited

U.S. PATENT DOCUMENTS 4,312,816 A * 1/1982 Aketa et al. ............... 558/354

* cited by examiner

*Primary Examiner*—James O Wilson
*Assistant Examiner*—Ebenezer Sackey
(74) *Attorney, Agent, or Firm*—Ladas & Parry LLP

(57) ABSTRACT

The present invention relates to an environmentally benign process for the preparation of (S)-α-cyano-3-phenoxybenzyl-(S)-2-(4-chlorophenyl)isovalerate from its diastereomeric mixture (RS)-α-cyano-3-phenoxybenzyl-(S)-2-(4-chlorophenyl) isovalerate.

39 Claims, 1 Drawing Sheet

PROCESS FOR PREPARING (S)-ALPHA-CYANO-3-PHENOXYBENZYL-(S)-2-(4-CHLOROPHENYL)-ISOVALERATE

FIELD OF INVENTION

The present invention relates to an environmentally benign process for the preparation of (S)-α-cyano-3-phenoxybenzyl-(S)-2-(4-chlorophenyl)isovalerate from its diastereomeric mixture (RS)-α-cyano-3-phenoxybenzyl-(S)-2-(4-chlorophenyl) isovalerate. More particularly, the present invention deals with the method for preparation of diastereomeric mixture of (RS)-α-cyano-3-phenoxybenzyl-(S)-2-(4-chlorophenyl)isovalerate (herein after referred as diastereomer-A) and its subsequent conversion to (S)-α-cyano-3-phenoxybenzyl-(S)-2-(4-chlorophenyl)isovalerate (hereinafter referred as S,S isomer), the most biologically active isomer of racemic fenvalerate via the crystallization induced dynamic kinetic resolution. The method provides a process for preparation of S,S isomer besides effectively converting the undesired isomer (R)-α-cyano-3-phenoxybenzyl-(S)-2-(4-chlorophenyl)isovalerate (hereinafter referred as SR isomer) via epimerization of the alcohol moiety using inexpensive catalyst to a desired diastereomeric mixture. Thus the method provides a simpler and efficient process for the industrial preparation of the biologically active SS isomer obviating the use of costly reagents such as cyclic dipeptides, enzymes as described in the prior art. This method also provides a route to green process in the sense that the undesired SR isomer is converted to a useful entity within the process parameters thus reducing chemical burden on environment

BACKGROUND OF THE INVENTION

As regards of SS isomer of general formula (I)

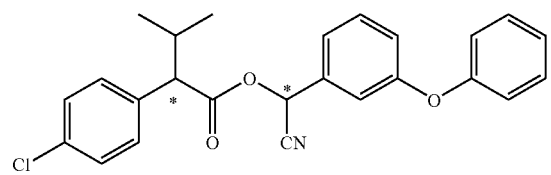

I

Where the * indicate asymmetric carbon atom having "S" configuration on both acid and alcohol moieties is of great interest, as the resolved isomer, esfenvalerate (SS) is biologically most active and has fourfold higher insecticidal activity than that of racemic fenvalerate a commercially important synthetic pyrethroid. An economically viable process for its preparation (SS isomer) is of great utility as it eliminates use of large quantity of a.i., thereby reducing chemical burden on environment.

Reference is made to EP Patent application 0,040,991 wherein a method for preparation of an enantiomeric pair (SS-RR) having insecticidal activity is described. The main draw-back of this process is that it yields a pair of enantiomers (SS-RR) instead of a single stereo isomer (SS).

Reference is made to the Patent application DE 2830031 wherein the process for preparation of esfenvalerate from its diastereomeric mixture is described. It describes a method for crystallization of SS isomer with or without using catalyst by four different processes.

The method A describes a process wherein SS isomer is crystallized without using a catalyst. The method B describes a process where in epimerisation at asymmetric carbon atom of alcohol moiety is effected by using a protic solvent or/and base catalyst. The method C describes a process wherein mother liquor after separating SS isomer is subjected to epimerisation with or without a catalyst. The method D performs the same procedure as in method C using a catalyst.

The main draw back of this process is that it employs protic solvents like methanol, ethanol with bases viz triethylamine, ammonia at temperature 0° C. to −5° C. At this temperature decomposition of the product, along with side reactions is observed. Another draw back is that the experimental conditions described are not completely reproducible albeit the procedure described is strictly followed.

EP patent 0050521, by Sumitomo Chemical Company Ltd. Japan, claims a method for preparation of SS isomer starting from a super saturated solution of diastereomeric mixture having respectively S configuration on acid moiety and (S), (R) configuration on Alcohol moiety using pure seed crystal solution of S-S isomer in presence or absence of basic catalyst. However the method could not be reproduced with consistency albeit the experimental conditions are followed as described in the patent.

Another drawback of this method is that when base catalyst like ammonia, triethylamine is used as described in experimental procedure of the patent, many a time product degeneration is observed in contrast to the crystallization of SS-isomer.

Preparation of (S)-α-cyano-3-phenoxy benzylalcohol by different methods viz. cyclic dipeptide, enzymes are known in prior art, reference is made to U.S. patent application Ser. No. 4,526,727 wherein a process is described for synthesis of (S)-α-cyano-3-phenoxy benzylalcohol using cyclic dipeptide, cyclo (D-phenylalanyl-D-histidine) and its subsequent esterification with (RS)-2-(4-chlorophenyl)isovaleric acid or its reactive derivatives to form a diastereomeric ester, followed by crystallization in a protic solvent to obtain SS isomer. The draw back of this process is that though cyclic dipeptide catalyst is used to synthesise the desired (S)-alcohol, the scale up operations for these processes are not yet commercially viable. Yet another draw back is that the process described for synthesis of the di peptide depend upon many physical characteristics like non-crystallinity, cohesiveness of the cyclic dipeptide which require stringent controls in preparation of the cyclic di peptide and are difficult to attain on scale up process leading to restriction of process parameters on a multi kilo scale preparation. Reference is made to U.S. patent application Ser. No. 5,177,242 where in a method to prepare optically active (S)-cyano-3-phenoxy-benzylalcohol by reacting corresponding aldehyde with hydrocynic acid using an enzyme S-oxynitrilase immobilized on a membrane is described.

The draw back of this method is that though it may be performed with reasonable success on a laboratory scale, it is difficult to obtain the enzyme of desired activity, level on a multi scale operations as the enzyme activity is variant w.r.t. source of its isolation.

Another disadvantage of this method is the stringent physical parameters to be maintained for immobilization of enzyme on the membrane with out effecting denaturation may practically pose problems on a commercial process.

OBJECTS OF THE INVENTION

The main object of the present invention is to develop a process for production of SS isomer [(S)-α-cyano-3-phenoxybenzyl-(S)-2-(4-chlorophenyl)isovalerate].

It is another object of the invention to provide a process for preparation of diastereomeric mixture of (RS)-α-cyano-3-phenoxybenzyl-(S)-2-(4-chlorophenyl) isovalerate (hereinafter referred as diastereomer-A) in an effective manner which consistently yields the desired isomer on crystallization.

It is another objective of the invention to utilize an inexpensive catalyst to convert the undesired isomer (R)-α-cyano-3-phenoxybenzyl-(S)-2-(4-chlorophenyl)isovalerate (hereinafter referred as SR Isomer) via epimerisation of the alcohol moiety to useful entity.

A further objective of the invention is to provide an environmentally benign process for production of biologically active SS isomer avoiding costly reagents known in prior art.

A further object of the invention is to provide a process for conversion of undesired isomer into useful entity with in the process parameters and recycle it to the processes of crystallization, thus reducing chemical burden on environment resulting in enhancing cost effectiveness of the process.

SUMMARY OF THE INVENTION

The present invention relates to an environmentally benign process for the preparation of (S)-α-cyano-3-phenoxybenzyl-(S)-2-(4-chlorophenyl)isovalerate from its diastereomeric mixture (RS)-α-cyano-3-phenoxybenzyl-(S)-2-(4-chlorophenyl) isovalerate.

DETAILED DESCRIPTION OF THE INVENTION

Figure 1:
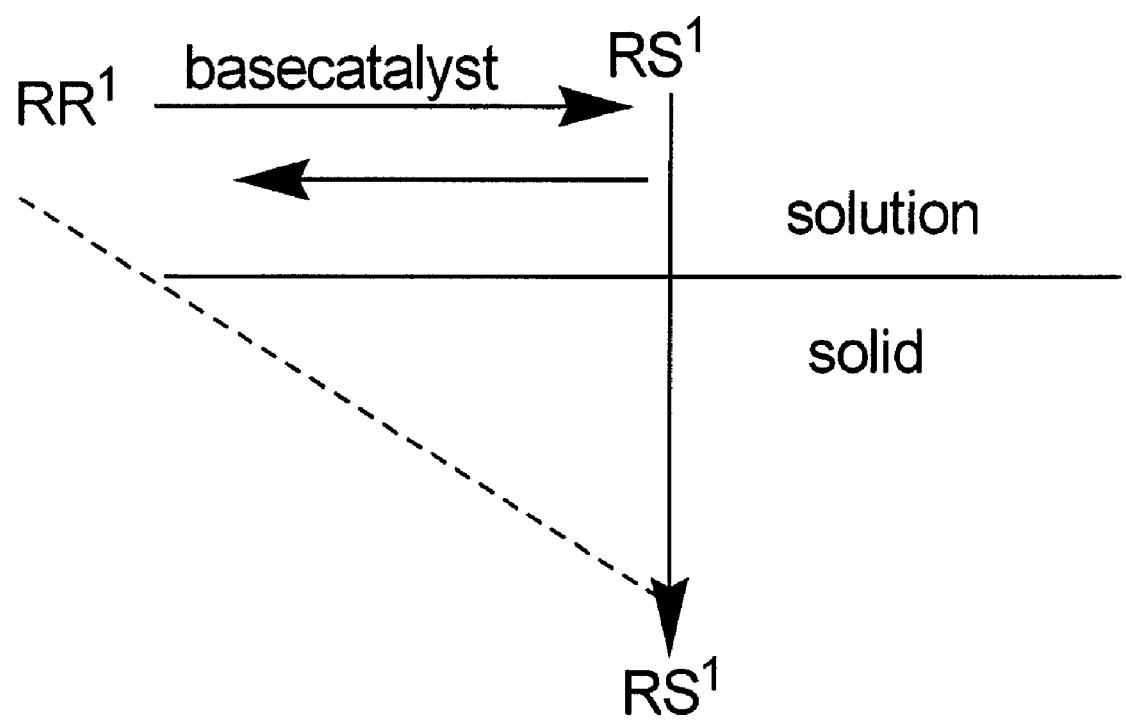
FIG. 1 illustrates a second-order asymmetric transformation.

Accordingly the present invention provides a process for manufacture of (S)-α-cyano-3-phenoxybenzyl-(S)-2-(4-chlorophenyl)isovalerate which comprises preparation of a diastereomeric ester (RS)-α-cyano-3-phenoxybenzyl-(S)-2-(4-chlorophenyl)isovalerate (diastereomer-A), a supersaturated solution of which in a hydrophilic organic solvent like alcohol having 1-5 carbon atoms in presence of pure SS seed crystals on controlled crystallization yields the desired SS isomer which was separated and the mother liquor enriched with unwanted SR isomer was epimerised and recycled into further batches of crystallization.

In one embodiment of the invention, the diastereomeric ester (Diastereomer-A) is prepared either by addition of (S)-2-(4-chlorophenyl) isovaleroyl chloride to aqueous solution (RS)-α-cyano 3-phenoxybenzylalcohol or addition of a premixed solution of (RS)-3-phenoxybenzaldehyde and (S)-2-(4-chlorophenyl) isovaleroyl chloride to aqueous solution of sodium cyanide under PTC conditions, more preferably by addition of (S)-2-(4-chlorophenyl)isovaleroylchloride to aqueous solution of (RS)-α-cyano3-phenoxybenzylalcohol under PTC conditions.

In another embodiment of the invention the choice of solvent is selected from the group consisting of aromatic hydrocarbon, chlorinated hydrocarbons like toluene, benzene, hexane, chloroform, 1,2-dichloroethane, dichloromethane respectively, more preferably 1,2-dichloroethane.

In another embodiment of the invention the phase transfer catalyst is quarternary ammonium salt selected from the group consisting of tertabutylammoniumbromide (TBAB), tertiarybutylammoniumhydrogensulphate (TBAHS), Benzyltriethylammonium chloride (TEBA) benzyltributylammoniumchloride, N-butyl-N,N-dimethyl-α-phenylethylammoniumbromide.

In yet another embodiment of the invention, the quaternary ammonium salt is tetrabutylammoniumbromide.

In yet another embodiment of the invention, sodium cyanide is used in amount of 1.0 to 1.60 mole per mole of 3-phenoxybenzaldehyde.

In further embodiment of the invention, (S)-2-(4-chlorophenyl). isovaleroylchloride is used in amount of 1.0 to 1.03 mole per mole of 3-phenoxybenzaldehyde.

In yet another embodiment of the invention, the (S)-2-(4-chlorophenyl) isovaleroyl chloride is added over a period of time ranging from 100-120 minutes.

In yet another embodiment of the invention, the (S)-2-(4-chlorophenyl) isovaleroylchloride is added to an aqueous solution of (RS)-α-cyano-3-phenoxy benzylalcohol at a temp. ranging from −2° C. to −4° C.

In another embodiment of the invention the course of the esterification reaction is followed by HPLC analysis drawing samples at intervals of time ranging from 30-90 minutes.

In a further embodiment of the invention, the reaction is continued after addition of acid chloride for a further period of time ranging from 60-120 minutes.

In a further embodiment of the invention, the diastereomeric ester formed (dilute-diastereomer-A) is concentrated under pressure ranging from 80-60 mm Hg to obtain diastereomer-A.

In another embodiment of the invention, the solvent recovered from distillation of dilute diastereomer-A is recycled for further batches of diastereomer-A formation.

In another embodiment of the invention, the diastereomeric ester (diastereomer-A) is subjected to the process of crystallization either by equilibration at a temperature range of 200°-220° C. under vacuum ranging from 100-50 mm Hg or without such operation more preferably without equilibration, by preparing a saturated solution in an organic solvent or solvent mixtures thereof and cooling the solution in such a manner that when seed/slurry of SS isomer is introduced, the added crystals remain thereafter in solution, in undissolved state and only crystals of required isomer (SS) alone crystallizes from the solution.

In yet another embodiment of the invention, the process of crystallization is controlled by predetermined rate of cooling the solution to a temperature range and maintaining the solution at that temperature range for sufficient period such that the rate of crystallization of SS isomer is conspicuous and the process is continued for sufficient period of time, till the crystallization of desired SS isomer is completed as indicated by enrichment of SR isomer in supernatant liquid.

In yet another embodiment of the invention, the progress of crystallization is monitored by chiral HPLC analysis, drawing samples at regular intervals of time to find the enrichment of SR isomer.

In yet another embodiment of the invention, the process of crystallization is stopped when the analysis of SR isomer is in the range of 50-55%.

In a further embodiment of the invention, the process of crystallization is preferably increased either by stirring or shaking the solution more preferably by stirring.

In another embodiment of the invention, the process of crystallization can be carried out at a temperature range +10° C. to −15° C. and most advantageously at a range of +2° C. to −8° C.

In another embodiment of the invention, the reaction time is such that it should be adequate to ensure that desired product (SS-isomer) of sufficient purity is obtained, generally in the range of 24-80 hrs more preferably 30-60 hrs.

In yet another embodiment of the invention, the organic solvent selected is from the group comprising of lower alcohols and/or aromatic aliphatic hydrocarbons or mixtures thereof.

In another embodiment of the invention, the solvent is selected from alcohols consisting of methanol, ethanol, isopropanol and hydrocarbon solvents like Hexane, Toluene, Heptane.

In another embodiment of the invention, the solvent is more preferably lower alkanol like methanol.

In another embodiment of the invention, the concentration of the diastereomer-A in solution is preferably in the range of 12-40% w/w w.r.t. solvent and more preferably in the range of 12-30%.

In further embodiment of the invention, the mother liquor enriched with SR isomer obtained after separation of the desired SS isomer is concentrated under reduced pressure to remove the solvent and then heated to a temperature of 50°-90° more preferably at 60°-70° C. under vacuum for a period of 1-4 hrs more preferably 2-3 hrs, cooled to room temperature and subjected to process of crystallization to obtain further quantity of the desired isomer (SS)-isomer.

In another embodiment of the invention, the mother liquor enriched with SR isomer is treated with a catalyst to effect equilibration of the isomers thus conveniently avoiding the tedious process of concentration of the mother liquor and subsequent heating thus reducing reaction times. The equilibrated mother liquor having almost equal ratio's of both isomers (SS:SR) is further subjected to process of crystallization of desired (SS) isomer.

In another embodiment of the invention, the mother liquor equilibrated is replenished with an amount of diastereomer-A equivalent to the weight of SS isomer obtained from process of crystallization and further subjected to process of crystallization maintaining the same concentration of the solution. This process is iterative and continued till crystals of SS isomer is obtained, thus, quite advantageous from the commercial point of view.

In another embodiment of the invention the catalyst employed for equilibration can either be organic or inorganic bases like alkali and alkaline earth metal hydroxides and carbonates like sodium hydroxide, potassium hydroxide, sodium carbonates and nitrogen containing bases like ammonia, dimethylamine, triethylamine, quaternary ammonium hydroxide like tetrabutylammoniumhydroxide, triethylbenzyl ammonium chloride or optically amines like (−) phenylethylamine or halides of alkali metals or ammonium halides. The more preferred base being fluorides of alkali metals or ammonium halides most preferably potassiumfluoride.

In yet another embodiment of the invention, with regard to the quantity of catalyst used it can be employed in the range of 2-10 mole %, more preferably in the range of 4-6 mole % w.r.t. the SR enriched mother liquor.

The process of the invention involves the preparation of diastereomeric mixture (diastereomer-A) in such a manner when it is subjected to process of crystallization, only crystals of SS isomer precipitates out and the mother liquor enriched with undesired isomer (SR isomer) is epimerised using an inexpensive catalyst and recycled to the process of crystallization in an iterative manner till crystals of SS isomer is obtained. In this quest for development of a suitable technology, a comprehensive search for solvent system and catalyst was undertaken to circumvent the problems encountered in referred EP 0,050,521. The results are tabulated in Table-1.

Despite many methods known in literature for the preparation of (S)-α-cyano-3-phenoxy benzylalcohol-(S)-2-(4-chlorophenyl)isovalerate, they have not yet been developed to the level where they can be carried out in an economic manner. In the present method of crystallization induced dynamic kinetic resolution (CIDKR), the SR isomer enriched mother liquor is epimerised at the benzyllic carbon atom using inexpensive catalyst and iteratively subjected to the process of crystallization by replenishing with fresh diastereomer-A equal to the quantity of SS isomer obtained. This approach is more practicable and quite appealing for small preparations (mg g) to pilot and process scale production (kg tonnes).

Many a time the results obtained from crystallization experiments as performed following the procedure described in EPO 0,050,521 are not reproducible albeit the conditions described therein are adhered to without deviation. Several modifications like varying of concentration of diastereomer-A, solvents, addition of additives like FeO, $H_3PO_3$, glacial acetic acid, process impurities like methyl ester of (S)-2-(4-chlorophenyl)isovalericacid, PTC catalyst, mother liquor were incorporated to the crystallizing solution of diastereomer-A as described in experimental part without any success in obtaining the required SS isomer in a consistent manner. Physical parameters like heating the diastereomer-A at temperatures ranging from 60°-120° C. and subsequent crystallization showed improved measure of success, though not to the manner where it can be useful entity on an industrial scale. Hence, a re-visit to the preparation of diastereomer-A (Table-2) was resorted to, and attempts were directed to modify the procedure of diastereomer-A preparation. In the present process a solution of (S)-2-(4-chlorophenyl)isovaleroylchloride in dichloroethane was added to a preformed solution of (RS)-α-cyano-3-phenoxybenzylalcohol, and after usual work up, this diastereomer-A was subjected to crystallization induced dynamic kinetic resolution (CIDKR) as such without resorting to any further operations like heating under vacuum etc., thus more importantly saving energy. The crystallization process can be performed at relatively high temperature than described in prior art.

In an embodiment of the invention, the process of crystallization of diastereomeric mixture (diastereomer-A) is performed via a phenomena known as crystallization induced dynamic kinetic resolution. It is known that enantiomers/diastereomers of compounds possessing acidic hydrogen atom on an asymmetric carbon atom can be epimerized with bases. In this process they pass briefly through the flat state. [P. Sykes; Explanations of reactions—methods and criteria of organic reaction mechanisms; verlag chemie 1973, page 133, and D. J. Cram. Fundamentals in Carbanion Chemistry, page 85-105, [Academic Press 1965] which is also observed in the case of the readily base catalyzed epimerisation of optically active mandelic acid nitrile (a) and of the corresponding methylether (b) to the racemic compounds.

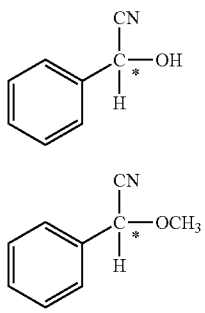

It is also known that formation of inter convertible diastereomers may lead to the preferential and possibly even to sole crystallization of one of the two isomers. The necessary instability of the compounds (species) involved in this special type of crystallization process may however, also make the isolation of pure enantiomer or diastereomers difficult. In spite of this potential draw back, the use of crystallization induced asymmetric transformation is very appealing, particularly when separations are attempted on industrial scale. It is observed that when two diastereomers in a mixture which are related as epimers in a super saturated solution are in equilibrium (FIG.1) the presence of base catalyst causes epimerisation of a diastereomer at chiral carbon which has acidic hydrogen as in the case of synthetic pyrethroid esters bearing cyano group on chiral carbon, the diastereomeric equilibrium is continually displaced by slow crystallization of one of the two species upon addition of homochiral crystals of an isomer. The species which crystallizes is not necessarily that which predominates at equilibrium. This phenomena is described as crystallization induced asymmetric disequilibration in which the rate of crystallization of less soluble diastereomer is slower than the rate of equilibration of the two species in solution. This phenomena known as crystallization induced asymmetric transformation of second order even though the work "order" is improperly used, the correct meaning in context is kind as asymmetric transformation of second kind.

The diastereomeric ester (diastereomer-A) is prepared either by reaction of aqueous sodium cyanide with a premixed solution of 3-phenoxybenzaldehyde and (S)-(+)-2-(4-chlorophenyl)-isovaleroylchloride or by reaction of the acid chloride with a preformed α-cyano-3-phenoxybenzylalcohol under PTC conditions more preferably by latter method to obtain a diastereomeric ester which consistently yields the crystals of desired isomer (SS) on crystallization.

The esterification is carried out in a solvent system selected from the group consisting of chlorinated hydrocarbons, aliphatic hydrocarbons, aromatic hydrocarbons like chloroform, dichloromethane 1,2-Dichloroethane, hexane, heptane, octane, toluene, benzene respectively more preferably, 1,2-Dichloroethane using PTC catalyst belonging to quaternary ammonium salt selected from the group consisting of tetrabutyl ammoniumbromide (TBAB), tetrabutylammoniumhydrogensulphate (TBAHS), Benzyltriethylammoniumchloride (TEBA), Benzyltributylammoniumchloride, N-butyl-N,N, dimethylphenylethylammoniumbromide, more preferably tetrabutylammonium bromide by addition of 3-phenoxybenzaldehyde to an aqueous solution of sodium cyanide at ambient or low temperature followed by the addition of (S)-2-(4-chlorophenyl) isovaleroyl chloride over a period of time ranging from 60-180 minutes more preferably from 90-120 minutes at a temperature range of −6° to +4° C., more preferably −3 to 0° C. under stirring, preferably maintaining the temperature of reaction for a further period of time ranging from 60-120 minutes after reaction, following the course of the reaction by HPLC analysis, drawing samples at intervals of time ranging from 30-120 minutes. The diastereomeric ester (diasteromer-A) formed is recovered from its dilute solution by stripping of the solvent under vacuum (80-60 mm Hg) and purging Nitrogen gas to ensure complete removal of the last traces of the solvent.

The diastereomeric ester (diastereomer-A) thus obtained is subjected to crystallization in a saturated solution containing solvent/solvent mixtures selected from the group comprising of lower alcohols and/or aromatic, aliphatic hydrocarbons and mixed solvents thereof, preferably alcohols containing 1 to 5 carbon atoms such as methanol, ethanol, isopropanol, aromatic hydrocarbons benzene, toluene, aliphatic hydrocarbons, hexane, heptane, octane, more preferably methanol in a concentration in the range of 12-40% w/w more preferably in the range of 12-30% w/w by following a programmed rate of cooling viz stepwise decreasing the temperature to 20° C. from ambient temperature, thereby cooling to 10° C. at intervals of time preferably 2-8° C. per hour more preferably 4-6° C. per hour. At this temperature (10° C.) pure crystals of SS isomer or slurry more preferably pure crystals (SS isomer) is introduced, wherein the added crystals/slurry remain in solution in undissolved state, decrease in temperature is continued to reach the onset temperature of crystallization at the rate of 2-1° C. per hour preferably 1° C. per hour and maintained around the onset of crystallization (2-5° C.) wherein the crystallization of SS isomer is conspicuous.

Further decrease in temperature is effected by maintaining the solution at a temperature range of +2 to 18° C. for a sufficient time ranging from 24-72 hrs, preferably 24-36 hrs by shaking or stirring the solution preferably stirring until crystallization is substantially completed as indicated by chiral HPLC analysis wherein samples of supernatant liquid indicate enrichment of undesired SR isomer. The crystallization process is stopped when SR isomer is in the range of 50-55% separating the crystals of SS isomer from solution either by filtration, decantation, or centrifugation, more preferably by filtration.

The mother liquor separated from the desired SS isomer is either concentrated under reduced pressure and heated to 60°-70° C. under vacuum for 2-3 hrs and subjected to process of crystallization or the mother liquor is epimerised using either an organic or inorganic base catalyst, which is stable under reaction conditions, examples include nitrogen containing bases like Ammonia, Triethylamine, 1-naphthylamine, quinoline, quaternary ammonium hydroxides like TEBA, TBAH also useful are inorganic bases like alkali and alkaline earth metal hydroxides carbonates, halides more preferably potassium fluoride in 2-10 mole % by heating generally for 4-6 hrs preferably 3-5 hrs till the ratio of two isomers is almost equal as indicated by chiral HPLC analysis. The contents are cooled and subjected to the process of crystallization or more conveniently the equilibrated mother liquor is replenished with an amount of diastereomer-A equal to the wt. of crystals of SS isomer obtained in earlier cycle and subjected to process of crystallization as described above. This step is iterative and continued by addition of diastereomer-A each time till crystals of SS isomer is obtained.

Thus consecutively using the equilibrated mother liquor of one cycle in another cycle as such avoids many process steps and enriching mother liquor with diastereomer-A to the extent of crystals (SS isomer) obtained maintains the saturated state of solution as also the catalyst is reused more often, with out isolation. By the use of combined enrichment and crystallization process, all the desired isomer (SS) may be effectively recovered from the diastereomeric mixture (diastereomer-A).

The following examples are given by way of examples and therefore should not construed to limit the scope of the present invention.

EXPERIMENTAL

Part-A

Example-1

Preparation of (RS)-α-cyano-3-phenoxybenzyl-(S)-2-(4-chlorophenyl) isovalerate (diastereomer-A):

81.37 gms of NaCN and 815.5 gms of water is charged into a suitable reactor equipped with cooling system, mechanical stirrer, dropping funnel and thermometer. The contents are mixed well and 49.6 g of dichloroethane and 10.2 gms of tetrabutylammonium bromide is charged into the reactor under stirring and cooled to +5° C. 246.98 g of (S)-(+)2-4(-chlorophenyl)isovaleroyl chloride and 205.4 gms of metaphenoxybenzaldehyde was mixed with 803 ml of dichloroethane and added over a period of 90 mts. through a dropping funnel under vigorous stirring. The temperature of the reaction mixture was maintained at +4° C. for a further period of 4 hrs and brought to room temperature. The organic layer (DCE) is separated out and washed with distilled water (3×200 ml) till pH of aqueous layer is neutral. The dilute organic layer (DCE) is concentrated to obtain crude ester (diastereomer-A) of composition of SS:SR ratio 46:48 in 95% yield.

Wt. of ester=441.5
Ratio of SS:SR=46:48

This material is used for preferential crystallization of esfenvalerate.

Example-2

10 gms of diastereomer-A of having SS/SR ratio 46.1/48.4 is dissolved in 13.13 gms of Heptane, toluene mixture containing 10% of toluene by heating and transferred to a suitable R.B flask provided with thermovel, and stirrer. At room temperature the solution was turbid to which 7.0 g of methanol was added and cooled to −16° C. under stirring for about 65 hrs. by adding a seed crystal (99.3) of SS-isomer at −13° C. at the end of which a viscous mass was observed. No preferential crystallization was noticed.

Wt. of crude=10.0 gms
% purity of SS isomer=46.1

Example-3

To 9.84 of liquid diastereomer-A was added 17.76 gms of methanol to form a 35% w/w solution of diastereomer-A which was refluxed for 1 hr at 65° C. and cooled to room temperature. The resulting solution was subjected to crystallization by cooling in a cryogenic bath to +6° C. A seed crystal of SS isomer of 99.9% purity was added to the solution at 15° C. and process of crystallization was continued for 18 hrs. at 6° C. The crystals obtained were filtered off.

Wt. of crystals=8.86
% purity of SS-isomer=46.57
Wt. of ML=16.31 gms

Example-3A

The mother liquor obtained (16.3 g) in the above example-3 was further subjected to the crystallization by adding a seed crystal at 2° C. and the process of crystallization was continued for 22 hrs. at +6° C. At the end of which the crystals obtained were filtered off and analyzed.

Wt. of crystals=0.51 g
% purity of SS-isomer=95

Example-4

52.2 gms of liquid diastereomer-A of Fenvalerate was dissolved in 110 g of Methanol to obtain a solution of 32% w/w diastereomer-A which was refluxed for 1 hr and cooled to room temperature. The solution was filtered off and cooled under stirring form 23° C. to −15° C. A seed crystal of pure SS-Isomer of 99% purity was introduced into the system at −14° C. The process of crystallization is continued for a period of 170 hrs at the end of which the crystals obtained were separated and filtered off.

Wt. of crystals=20.0 g
% purity of SS-isomer=42.89
Wt. of ML=115.86 gms

Example-4A

The ML of example 4 (115.88 g) is concentrated and divided into two parts. To 10.7 gms of Diasdtereomer-A was added 14.6 gms of heptane toluene mixture of composition as described in example-2 and refluxed for 2 hrs. The contents were cooled to room temperature and 7.7 g of methanol was added and cooled to −10° C. in a cryogenic bath. A scoop of seed crystals of SS isomer of 99.9% was added at −10° C. The solution was cooled to −14° C. and maintained at that temperature for 144 hrs. The precipitated crystals were removed by filtration and ML was separated out.

Wt. of crystals=0.9 g
% purity of SS isomer=98

Example-5

To 19.96 gms of liquid diastereomer-A obtained from ex-1 was added 61 ml of MeOH heated to reflux, cooled to room temperature and filtered off. The solution was cooled in a cryogenic bath under stirring by setting the temperature to −15° C. seed crystals of SS-Isomer (99.3%) was introduced after temperature reached to −15° C. and further cooling was continued for 96 hrs. At the end of which the precipitated crystals were separated out.

Wt. of crystals=9.2$^2$ g
% purity of SS-isomer=45.2%
Wt. of ML=87.20 gms

Example-5A

The ML obtained from the above example-5 was further subjected to crystallization by cooling to −15° C. At −11° C. a slurry of seed crystals (0.07248 g; 99%) of SS-isomer was introduced. The solution is stirred at −15.5° C. for a period of 96 hrs. The separated out crystals were weighed and air dried.

Wt. of crystals=6.80 g
% purity of SS-isomer=57.1

Example-6

20.0 g of Mother liquor obtained from experiments where no preferential crystallization has not occurred was dissolved in 143 gms of Methanol to obtain a 12% w/w solution of diastereomer-A and subjected to process of crystallization by cooling to −8° C. under stirring in a reactor with a provision for temperature recording and addition of seed crystals. A seed crystal of 99.3% of SS-Isomer was introduced at −8° C., followed by 4 ml of (6% w/w) methonolic ammonia. The cooling at −8° C. was continued for 87 hrs and solids obtained were analyzed for SS-isomeric content.
Wt. of crystals=7.40 g
% purity of SS-isomer=97.45%
Wt. of ML=155.88 g

Example-7

The mother liquor obtained from above example-6 was subjected to preferential crystallization as described below:

7.36 g of diastereomer-A obtained after concentration of Mother liquor (155.8 g) from above example-6 was dissolved in MeOH to obtain a 12% solution of diastereomer-A which was cooled under stirring in a cryogenic bath from +4° C. to −15° C. 2.3 ml of methonolic ammonia of 6% (w/w) was introduced into the system at −4° C. followed by SS-isomer seed crystal (99%). The process of cooling is continued for a period of 42 hrs and the crystals obtained were separated out.
Wt. of crystals=2.95 g
% purity of SS-isomer=98.4%

Example-8

16.07 g of solids of isomeric ratio of SS:SR (1:1) obtained from experiments 30, 33, 34 (Table-1) was dissolved in MeOH to get a solution of 12% and subjected to crystallization in a cryogenic bath by cooling from room temperature to −5° C. A pure seed crystal of SS-isomer (99%) was introduced at 0° C. followed by 3.2 ml of 6% w/w methanolic ammonia. The solids obtained were filtered off at the end of 94 hrs and analyzed.
Wt. of crystals=8.86 g
% purity of SS-isomer=43.2%
Wt. of ML=116.4 gms

Example-9

5.14 g of diastereomer-A was dissolved in MeOH to obtain 12% solution. To the above solution 0.06 g (2 mol %) of TBAOH (tetrabutylammoniumhydroxide) was added and cooled to −5° C. At that temperature a seed crystal of SS-isomer (99.3%) was introduced into the system and further cooling was subjected in a stepwise manner to −17° C. (−5° C. for 18 hr; −10° C. for 24 hrs, −15° C. for 29 hrs and −17° C. for 40 hr) at the end of which the crystals obtained were filtered off and analyzed.
Wt. of crystals=0.81 g
% purity of SS-isomer=96.38%

Example-10

5.03 g of diastereomer-A was dissolved in MeOH to obtain 17.4% solution which was subjected to crystallization in a cryogenic bath at −15° C. to −18° C. for a period of 81 hrs by adding 2.0 ml of 6% methonolic ammonia and seed crystal (99.3%) at −15° C. The crystals obtained were separated.
Wt. of crystals=1.28 g
% purity of SS-isomer=92.9%

Example-11

23.25 gms of diastereomer-A whose composition consists of 5.0 g liquid diastereomer-A and the rest obtained from mother liquor of KR-92 (Table-1) was dissolved in 97.45 gms of MeOH to obtain 19.26 w/v solution which was subjected to cooling in a cryogenic bath from room temperature to −8.6° C. in 48 hrs. A seed of pure SS isomer (99.3%) was introduced at −8° C. followed by 10 ml of MeOH/NH$_3$ of 6% w/w. At the end of reaction time (48 hrs) 2.0 ml of acetic acid was added and the crystals obtained were separated out.
Wt. of crystals=1.16 g
% purity of SS-isomer=97.6%

Example-12

2.0 gms of diastereomer-A having SS:SR 45:46 ratio was mixed with 0.5 gms of SS-isomer and 22.5 g of MeOH was added to obtain 10% w/w solution of diastereomer-A which was enriched with 20% of SS isomer. This solution was subjected to crystallization under at a stepwise cooling from +5° C. to −3° C. by adding a seed crystal at 0° C. The process of crystallization was continued for a period of 147 hrs, at the end of which the crystals obtained gave a purity of 70% of SS-isomer.
Wt. of crystals=1.43 g
% purity of SS-isomer=69%
Wt. of ML=21.09

Example-13 a. In a suitable reactor provided with a provision for measurement of temperature was added 8.0 g of diastereomer-A and 12 g of heptane, toluene mixture (Hep:Tol=1: 1) to obtain 40% w/w solution. The solution was cooled to −5° C., a seed crystal of SS isomer (99%) was introduced and further cooling at that temperature was continued for 90 hrs. the crystals were separated out and analyzed for their SS-isomer content.
Wt. of crystals=0.1 g
% purity of SS-isomer=77.2%
Wt. of ML=20.46 b. The mother liquor (40%) was further subjected to crystallization following the procedure described above except that the solution was cooled to −13° C. for 240 hrs. the crystals obtained were separated out by filtration.
Wt. of crystals=2.85 g
% purity of SS-isomer=54.2%

Example-14

In a suitable reactor was placed diastereomer-A (36.33 g) obtained form the experiments where the preferential crystallization has not been achieved and methanol (2.38 g), and stirred well to obtain a 13% w/w solution of diastereomer-A. This solution was cooled in a cryogenic bath under stirring from +5° C. to −10° C. at the rate of one degree per hour. Seed crystal of SS-isomer (99.3%) was introduced into the system at −1° C. and further cooling after reaching −10° C. was continued for 36 hrs. The solids obtained were separated out by filtration and analyzed.
Wt. of crystals=13.31 g
% purity of SS-isomer=96.5

Example-15

In a 250 ml round bottom flask was placed 10.08 gms of diastereomer-A and 67.0 gms of a mixture of IPA and hexane (45:55) heated to reflux (90° C.) for 1 hr. The solution was cooled to room temperature, filtered into a 250 ml round bottom flask, having provision for temperature measurement, stirrer and cooled to 5° C. in a cryogenic programmed temperature bath. Further cooling from +5 to −10° C. was effected in such a manner that there was a decrease of one degree for every 60 minutes. A seed crystal of SS-isomer was added to the solution at +1° C. and cooling is continued till −10° C. After remaining at −10° C. for 24 hrs. The solids obtained were separated out and analyzed.
Wt. of solids=6.43 g
% purity of SS-isomer=49.83

Example-16

To 17.69 gms of concentrated, mother liquor obtained from experiments after separating the solids (SS:SR 1:1) was added 0.11 g of methyl ester, of (S)-2-(4-chlorophenyl)isovaleric acid, and 116 gms of methanol to obtain 13.3% w/w homogeneous solution of diastereomer-A and refluxed for 1 hr; The contents were cooled to room temperature and subjected to crystallization in a cryogenic bath by cooling in a stepwise manner from RT to +3° C. in 4 hrs. Further cooling was effected to −4° C. at the rate of 1° C. for 60 minutes. A seed crystal of SS-isomer (99.3%) was introduced at −2° C. The solution was held at −3° C. for a further period of 72 hrs at the end of which solids obtained were separated and analyzed.
Wt. of crystals=7.84 g
% purity of SS-isomer=44.5

Example-17

8.82 g of diastereomer-A (SS:SR 1:1) was mixed with 1.5 gm of mother liquor of earlier experiments and dissolved in methanol (55 g), heated to reflux for one hr to obtain 13.9% solution of diastereomer-A which was cooled to room temperature and transferred to a suitable reactor provided with thermovel to measure temperature and a stirrer. The stirred solution was cooled in a cryogenic bath at a stepwise rate of cooling of one degree centigrade for one hour from +50 to −7° C. Pure SS isomer (99.3%) was added to the cooling solution at +1° C. After keeping the solution at −7° C. for 1 hrs the solids obtained were filtered and separated.
Wt. of Solids=5.63 g
% purity of SS-isomer=45.23

Example-18

15.05 gms of diastereomer-A having ratio of SS:SR 45:48 obtained from unsuccessful experiment of preferential crystallization was dissolved in 101 gms of methanol to obtain a 13% solution of diastereomer-A to which 0.01 g of iron rust was added. This solution was subjected to crystallization in a 250 ml round bottom flask having provision for temperature recording and stirring by placing in a cryogenic bath and decreasing the temperature at the rate of +1° C./hr from +12° C. to −5° C. A slurry of seed crystals crystallized from pet ether was introduced into the system at +1° C. and further cooling is effected till temperature was reached to −5° C. The solution was held at −5° C. for a further period of 10 hrs. The crystals obtained at −5° C. were dissolved while filtering.
Wt. of crystals=0.63 g
% purity of SS-isomer=43.62
Wt. of ML=110.68

Example-19

15.04 g of diastereomer-A was equilibrated at 120° C. under vacuum for 2 hrs, cooled to room temperature and 95 gms of methanol was added to obtain 13.6% solution of diastereomer-A. This solution was subjected to crystallization, in a 250 ml round bottom flask fitted with a stirrer, a thermovel and an arrangement to add a slurry of seed crystals, by cooling the solution at a programmed rate from +10° C. to −13° C. at the rate of 1° C./3 hrs. When the temperature reached +10° C., slurry of seed crystals in hexane obtained by fresh crystallization of 200 mg of SS-isomer of 99.3% was added at once. After reaching −13° C. the solution was continued to be kept at that temperature for 48 hrs and the solids obtained were filtered off.
Wt. of crystals=2.13 g
% purity of SS-isomer=94.7
Wt. of ML=106.29

Example-20

Diastereomer-A having SS:SR in the ratio of 1:1 obtained from crystallization experiments wherein preferential crystallization has not taken place was pooled together and 13.0 g of that material was equilibrated at 120° C. for 2 hrs under vacuum (200-300 mm) and cooled to room temperature and was dissolved in 85 gm of MeOH to obtain a 13.0% solution of diastereomer-A. This solution was filtered off and transferred to a suitable reactor having provision for stirring, temperature measurement and introduction of slurry seed of crystals. This solution was gently stirred from +10° C. to −13° C. in a cryogenic bath following a rate of cooling of 1° C./3 hr after addition of about 200 mg of slurry of seed crystals (SS-isomer) and 100 mg iron rust at +10° C. After reaching −13° C. the solution was continued to be at that temperature for a further period of 52 hrs and crystals were separated out by filtration.
Wt. of crystals=2.13 g
% purity of SS-isomer=94.7

Example-21

60.0 g of diastereomer-A was equilibrated at 110° C. for 1½ hrs and cooled to room temperature. To the above liquid diastereomer-A was added 400 g of MeOH to obtain 13.0% solution. This solution was subjected to programmed rate of cooling 1° C./5 hr from +10° C. to +2° C. while introducing a seed crystal of SS-isomer (99.3%) at +10° C. under gentle stirring in a 500 ml round bottom flask by keeping in a temperature programmed cryogenic bath. After attaining the temperature of +2° C. the solution was further held at that temperature for 40 hrs. and crystals obtained were separated by filtration.
Wt. of crystals=1.67 g
% purity of SS-isomer=98.2

Example-22

10.0 g of diastereomer-A having a ratio of SS:SR in 1:1 was dissolved in 66 g of methanol to obtain 13.0% solution of diastereomer-A. This solution was subjected to crystallization by addition of slurry seed crystals in hexane at +10° C. and cooling the solution from that temperature to 4° C. in a phased manner while introducing 0.01 g of quinide at 6° C. and further cooling the reaction mass to 4° C. and holding the solution at that temperature for 36 hrs. At the end of which the crystals obtained were analyzed.
Wt. of crystals=0.95 g
% purity of SS-isomer=42.0

Example-23

10.0 g of diastereomer-A was equilibrated at 120° C. for 2 hrs and cooled to room temperature. To the liquid isomer-A was added 67.0 g of methanol to obtain 12.8% solution of diastereomer-A which was subjected to crystallization by addition of 0.33 g of glacial acetic acid and cooling the solution from +18° C. to +3° C. under stirring at a rate of cooling of 2° C./hr by addition of a slurry of seed of crystals (200 mg) at 14° C. After reaching +7° C. the solution was cooled to +3° C. at the rate of 1° C. per every 3 hrs. and held at that temperature for 48 hrs and the crystals were separated by filtration.
Wt. of crystals=3.46 g
% purity of SS-isomer=47.02

Example-24

99.5 gms of liquid isomer prepared on a 3.0 kg batch scale as described in example-1 was heated at 120° C. for 3 hrs and cooled to RT. Thus obtained material was dissolved in 618 gms of methanol to obtain 13.8 solution of diastereomer-A which was cooled at a programmed rate of 1° C./hr from −10° C. to −8° C. in a suitable reactor having provision for stirring, introduction of slurry seed and measurement of temperature slurry seed of crystals freshly crystallized in hexane of SS isomer were introduced at +8° C. Further cooling to −12° C. from −8° C. was affected at the rate of 1° C./3 hrs, after reaching −12° C. the solution was held at that temperature for 48 hrs and solids obtained were filtered off and analyzed.
Wt. of solids=1.39 g
% of SS-isomer=94.0
Wt. of ML=704.68

Example-25

The mother liquor of example-24 (704.68 g) after separating the 1.39 g of crystals was concentrated and made to a solution of 19.8% in methanol. 140.0 g of heptane was added to the solution and the programmed rate of cooling from +6° to −13° C. was continued by introduction of slurry seed of SS isomer at 5° C. as described in above example. The reaction mixture was kept at −13° C. for a period of 90 hrs. the separated crystals were analyzed for SS-isomer content by HPLC.
Wt. of solid: 9.54
% purity of SS isomer=97.5

Example-26

17.36 g of liquid isomer-A melted at 120° C. was dissolved in 90.3 g in methanol-toluene mixture (87:3.2) to obtain a 16.87% diastereomer-A solution. This solution was cooled from +20° C. to 14° C. at a programmed rate of cooling of 2° C./hr in a cryogenic bath while stirring and seeded with a crystal of 99.9% SS-isomer at +14° C. Further cooling from +14° C. to +2° C. was performed at the rate of +1° C./90 minutes. After reaching the temperature of +2° C. the solution was held at that temperature for a period of 12 hrs under gentle stirring. The crystals obtained are filtered and analyzed for SS-isomer content by HPLC.
Wt. of solids–7.05 g
% of SS-isomer=43.3 g

Example-27

20.0 g of diastereomer-A was equilibrated at 120° C. for 4 hr cooled to RT and made to 11.5% diastereomer-A solution in methanol-toluene mixture containing 3% of toluene. This solution was cooled from +15° C. to −6° C. in a suitable reactor provided with a stirrer, thermovel, and provision for introduction of seed crystals by placing in a cryogenic bath having programmed temperature cooling facility. A seed crystal of 99.3% of SS-isomer was added at +9° C. and cooling is continued from −6° C. at 1° C./hr. 1.0 ml of 9% w/w methonolic ammonia was added at −3° C. The solution was held at −6° C. for a period of 16 hrs and crystals were separated out and analyzed for SS isomer content.
Wt. of solids=6.7 g
% of SS-Isomer=42.27

Example-28

40.02 gms of diastereomer-A prepared on a 3.0 kg scale batch prepared according to procedure described in example-1 was dissolved in a mixture of Heptane (65 g), N,N-DEA (28.0 g) and hexane (18.9 g) to obtain 30% solution. Prior to this, the diastereomer-A was equilibrated at 120° C. for 4 hr as described in above examples. Thus obtained solution was cooled in an appropriate reactor having provision for seed crystal addition, thermovel and stirrer following a programmed cooling in a cryogenic bath at the rate of 1° C./hr from +10° C. to −10° C. A seed crystal of 99.3% of SS-isomer was added at +6° C. After reaching −10° C., the reaction mixture was held at that temperature for a further period of 24 hrs, at the end of which solids were separated by filtration.
Wt. of solids–2.54 g
% of SS-isomer=81.35

Example-29

10.26 g of diastereomer-A was dissolved in 31.26 gms of methanol to obtain a 25% w/w solution which was cooled in a reactor provided with a provision for seed crystal addition, thermovel and stirrer 0.03 g of tetrabutylammoniumbromide (TEBA) and 4.0 ml of glacial acetic acid was added at 21° C. followed by addition of pure SS-isomer crystals of 99.3%. Further cooling was followed by a temperature programme designated at the rate of 1° C./4 hr to +15° C. The solution was kept at that temperature for 19 hrs wherein growth of crystals was conspicuous and started increasing. At the end of 19 hrs at 15° C., the crystals were separated by filtration.
Wt. of solids–4.75 g
% of SS-Isomer=47.02

Example-30

10.04 gms of diastereomer-A was dissolved in 30 gms of MeOH to obtain 25.0%w/w solution. To which was added 0.520 g of fenvaleric acid and 0.018 g of PTC catalyst (TBAB) and refluxed for 2½ hrs. This solution was transferred to a suitable reactor provided with a stirrer, thermovel, provision for seed crystal addition and kept in a cryogenic bath for cooling from +25° C. to +19° C. at 1° C./2 hrs. A seed crystal was introduced at +19° C. After reaching +19° C. the solution was held at that temperature for 20 hrs. The crystals obtained were separated and analyzed for SS-isomer content.
Wt. of solids=4.4 g
% of SS-Isomer=46.88

Example-31

7.0 g of diastereomer-A recovered from earlier experiments having SS:SR (46:47) was equilibrated at 115° C. for 4 hrs and cooled to RT. This material was dissolved in 41.54 g of IPA:MeOH (10:30) mixture to obtain a 14.5% w/w solution of diastereomer-A which was subjected to preferential crystallization in a 250 ml round bottom flask fitted with a stirrer, thermovel to measure temperature and provision for addition of seed crystals. This solution was cooled in a cryogenic bath from +23° C., by decreasing temperature at the rate of 2° C. for every 3 hrs. A seed crystal of 99% purity of SS-isomer was introduced into the system at 20° C. and temperature was decreased hereafter at 1° C. for 2 hrs. It was observed that crystal was dissolved at 18° C. A fresh seed crystal was added to the solution at that temperature and process of crystallization was continued by decreasing temperature to 14° C., where in the increase of crystals was conspicuous and the solution was held at that temperature for 10 hrs and solids obtained were filtered off and analyzed for SS isomer content by HPLC.
Wt. of solids=2.8 g
% of SS-isomer=44.7

Example-32

279.0 g of diastereomer-A having SS:SR ratio 432:435 was equilibrated at 120° C. under vacuum (200-100 mm of Hg) for 2 hrs, cooled to room temperature and made to 29.9% w/w solution of diastereomer-A in methanol. This solution was transferred to a 2.0 lit round bottom flask equipped with a stirrer, thermovel and a provision for addition of slurry of seed crystals. This solution is cooled in a cryogenic bath under stirring at a temperature programme such that the rate of crystallization is conspicuous and continuous without getting abrupt crystallization, from +20° C. to +5° C. at the rate of 1° C./hr upto +12° C. wherein slurry of seed crystals of SS-isomer obtained from crystallization of SS-isomer in hexane was added together with mother liquor. After keeping the solution at 12° C. for 1 hr, further cooling is continued by decreasing the temperature at the rate of 1° C. while observing the process of crystallization once in 2 or 3 hrs. Thus after reaching 5° C. the solution was held at that temperature (5° C.) for 34 hrs and crystals were separated out and analyzed for SS-isomer content.
Wt. of crystals=49.44 g
% purity of SS-isomer=95.67
Wt. of ML=857.10 g Example-33

To the mother liquor obtained (857 g) from example example-32 was added 610 mg of KF and heated at 49° C. for 60 hrs and concentrated to 30% w/w solution and subjected to process of crystallization from +20° C. to 0° C. as described in above example and holding the solution for a further period of 72 hrs at 0° C. The crystals obtained were filtered off and analyzed for SS-isomer content by chiral HPLC.
Wt. of crystals=64.3 g
% purity of SS-isomer=65.23
Wt. of ML=670.84 g Example-34

The mother liquor (670.0 g) of example 33 was heated under stirring at 55° C. for 20 hrs, concentrated the solution to 30% w/w and kept for cooling in an appropriate reactor as used in above example following a temperature programme from +15° C. to −6° C. at the rate of 2° C./hr. initially i.e. from +15° C. to +12° C., where upon a slurry of seed crystals of SS-isomer (99.3%) prepared as described in above example was introduced into the system. The process of cooling was continued till the onset of cooling at the rate of 1° C./hr i.e. up to +4° C. Further cooling was continued to −6° C. by observing the rate of crystallization and decrease of temperature is performed in such a manner that it does not initiate abrupt crystallization. After keeping the solution at −6° C. for 24° C. hrs, the crystals obtained were found to form a lump which was dissociated by raising the temperature to +4° C. where in it was broken and the crystals were separated by usual manner as described in above examples.
Wt. of crystals=14.03 g
% purity of SS-isomer=89.79
Wt. of ML=518.2 g Example-35

The ML (518 g) obtained from example 34 was heated at 55° C. for 20 hrs and concentrated to 30% w/w solution of diastereomer-A and filtered before subjecting to the process of crystallization in a reactor as described in ex. KR-301 under programmed cooling from +15° C. to −10° C. following the procedure described in ex. KR-308. After attaining the temperature of −10° C., the solution was maintained at that temperature for 20 hrs. The solids were separated and analyzed for SS-isomer content by chiral HPLC analysis.
Wt. of solids=10.22 g
% purity of SS-isomer=95.63
Wt. of ML=857.10 g Example-36

The ML (857 g) obtained from example 35 was equilibrated at 55° C. for 4 hrs cooled, filtered and used for process of crystallization in a 1.0 lit round bottom flask provided with a thermovel, stirrer and provision for addition seed slurry. The reactor was cooled in a cryogenic bath, at a programmed rate of cooling from +22° C. to −10° C. by adding slurry a seed as prepared as described in ex. 301 was introduced at 8° C. Further cooling is done by decreasing the temperature while observing rate of crystallization at the rate of 1° C. for every 5 hrs till temperature is reached to −10° C. and holding the solution at that temperature for a further period of 50 hrs. At the end of which crystals were separated out, and analyzed for SS-isomer content.
Wt. of crystals=3.94 g
% purity of SS-isomer=93.9
Wt. of ML=429.06

TABLE

| Expt. No. | Wt. of Crystals (in gms) | % purity (SS isomer) |
|---|---|---|
| 32 | 49.44 | 95.67 |
| 33 | 64.3 | 65.23 |
| 34 | 14.03 | 89.79 |
| 35 | 10.02 | 93.63 |
| 36 | 3.94 | 93.9 |

Part B

Preparation of diastereomer-A

Example-37

8.32 g of NaCN and 78.8 gms of $H_2O$ was charged simultaneously into a 500 ml reactor equipped with a provision for cooling the reaction mass to −4° C. to −5° C., a mechanical stirrer, thermovel, dropping funnel and a vent tube. The contents are stirred well, Dichloromethane (80 g) and tetrabutylammonium bromide (1.08 g) was added to the solution while stirring after which metaphenoxybenzaldehyde (21.7 g) was added to the solution under stirring through a droping funnel over a period of 15 minutes at 20-25° C. minutes. This solution was cooled to −4° C. and 25.54 gms of (S)-(2)-(4-chlorophenyl)isovaleroylchloride diluted with 40 ml of dichloroethane was added, keeping the temperature between −1 to −4° C. in two hrs. the temperature of reaction mass was further maintained at that temperature for another two hrs during which period the reaction was monitored by chiral HPLC after which the reaction temperature was brought to room temperature and layers were allowed to separated out. The lower organic layer (DCE) was separated and washed thrice with (3×2000 ml) distilled water, each time checking the pH of aqueous layer, and continued washings if pH is not neutral. The upper aqueous layer (NaCN) is detoxified separately. The DCE layer is concentrated at 40° C.-50° C. at 35-40 mm of Hg and purged with nitrogen intermittently to yield 48.18 gm of diastereomer-A of composition SS:SR 43:87:46.44.

Example-38

20.2 g of the liquid diastereomer-A (SS/SR 45.2/45.5) prepared as described in the above example-37 is such without any further modifications by dissolving in 60.0 gms of methanol to obtain a 25% w/w solution of diastereomer-A. This solution was cooled in a suitable reactor equipped with a provision for seed crystal addition, thermovel and stirrer; by placing in a temperature programmed cryogenic bath in a stepwise manner from +20° C. to +15° C. at 2° C./hr. A slurry of seed crystals of SS isomer was added at +15° C. and solution was held at that temperature for 12 hrs. Further cooling was effected by decreasing temperature @ 1° C./hr till temperature reached to +7° C. The solution was held at 7° C. for 24 hrs and the crystals obtained were filtered off, analyzed for SS-isomer content by chiral HPLC.
Wt. of crystals=2.58
90% purity of SS-isomer=96.4

Example-39

106.79 gms of liquid diastereomer-A obtained following the procedure described in example 37 wherein a new PTC catalyst was used instead of TEBA. This material was dissolved in 430 gms of methanol in a 1000 ml round bottomed flask equipped with a stirrer, thermovel and provision for addition of seed crystal to obtain a into 32.35 (w/w) solution of diastereomer-A. This solution was cooled in a cryogenic bath under stirring following a programmed rate of cooling (from +20° C. to 16° C. in 2 hrs (2° C./hr) at the end of which temperature was decreased in one step to 7° C. and a seed crystals of SS-isomer (99.3%) was introduced into the reactor. Further cooling was effected from +7° C. to −7° C. at the rate of 1$^{+\circ}$ C./hr and the solution was kept at −7° C. for 60 hrs at the end of which the crystals obtained were separated by filtration, dried and analyzed for SS-isomer content.
Wt. of crystals=16.5 g
% purity of SS-isomer=95.2%
Wt. of ML=506.0 gms

Example-40

The mother liquor obtained in the above experiment (example 39) was equilibrated with 0.37 g of potassium thioxide at 63° C. for 18 hrs. cooled to room temperature and was replenished with 16.0 gms of liquid isomer-A as used in example above and made up to 19.7% w/w solution by adding 20.0 gms of methanol. The process of crystallization was repeated as described in above example except that instead of decreasing temperature from 16° C. to 7° C. at once it was effected at the rate of 4° C. per hr. and further cooling is done as described in above example upto −6° C. and the solution was held at that temperature (−6°) for 2 hrs. After separating the crystals, and ML, the crystals were analyzed by chiral HPLC for SS-isomers content.
Wt. of crystals=12.16
% purity=96.7%
Wt. of ML=515.84 g

Example-41

The ML (515.84 gms) of example 40 was equilibrated at 60° C. for 18 hrs at 65° C., cooled to room temperature and replenished with 16.0 gms of liquid diastereomer as used in above example and made upto 20% w/w solution by addition of 21 gms of methanol. This solution was subjected to crystallization by decreasing the temperature from 18° to 5° C. at the rate of 3° C./hr. and introducing SS-isomer (99.3%) seed crystal at 5° C. Further cooling to −8° C. was effected at the rate of 1° or 2° C. while observing the rate of crystallization. The solution was held at −8° C. for 24 hrs. The crystals obtained were separated out by filtration, dried and analyzed for SS-isomer content.
Wt. of crystals=11.0 g
% purity of SS-isomer=97.5
Wt. of ML=530.06 g.

Example-42

The mother liquor 530.06 gms obtained in above example-41 was equilibrated at 60° C. for 6 hrs cooled to room temperature and replenished with 15.8 gms of liquid diastereomer as used in above example and replenished with 23.0 g of methanol respectively to obtain 20% w/w solution of liquid diastereomer A. This solution was subjected to stepwise cooling following the method described in above example from +16 to +3° C., at which temperature (3° C.) seed crystals of SS-isomer (99%) was added and further cooling to −8° C. was continued by decreasing the temperature while observing the rate of crystallization in such a manner at the rate of 1° C./5 h upto −2° C. from +3° C. and there after at the rate of 1° C. for 90 minutes and holding the solution at −8° C. for 12 hrs at the end of which the crystals obtained were separated and analyzed by chiral HPLC for their SS-isomer content.
Wt. of crystals=11.33 g
% purity of SS=98.55
Wt. of ML=552.29 g Example-43

The ML (552.9) obtained in above example-42 was equilibrated for 10 hrs at 65° C., cooled and replenished with 15.07 g of liquid isomer as used for the above example and 15.0 g of methanol respectively to obtain a 20% w/w solution of diastereomer-A, which was subjected to step-wise cooling following the temperature programme as described in above example except that cooling was continued upto −11° C. and holding the solution between −10° C. to −11° C. for 48 hrs. The crystals obtained were separated by filtration and analyzed for SS-isomer content by chiral HPLC.
Wt. of crystals=6.91
% purity=95.9
wt. of ML=567.54 g

TABLE

| Expt. No. | Wt. of SS isomer (gms) | % purity |
|---|---|---|
| 39 | 16.5 | 96.5 |
| 40 | 12.16 | 96.7 |
| 41 | 11.0 | 97.58 |
| 42 | 11.33 | 98.5 |
| 43 | 6.91 | 95.9 |

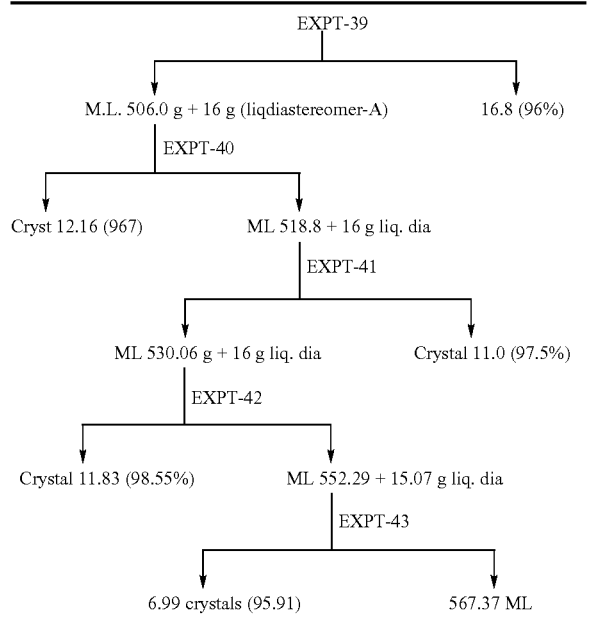

Example-44

51.4 g of liquid diastereomer-A prepared as described in example-37 except that instead of tetrabutylammonium bromide (TBAB) a new phase transfer catalyst N-butyl-N,N dimethyl-α-(S)-phenyl ethylammoniumbromide, was used and dissolved in 104.45 g of MeOH to obtain a 33% w/w solution of diastereomer-A. This solution was transferred to a 500 ml round bottom flask equipped with a thermovel, stirrer and provision for addition of slurry seed and cooled in a cryogenic bath from +20° to +8° C. at the rate 2° C./hr till temperature is reached to +13° C., at which a slurry seed crystals of SS-isomer (99.3%) crystallized from SS-isomer in hexane together with mother liquor was introduced into the system. Further cooling to +8° C. is effected at the rate 1° C./4 hrs and the solution was held at that temperature for 20 hrs and filtered. The crystals obtained were analyzed for SS-isomer content.
Wt. of crystals=11.2 g
% purity of SS-isomer=95.3
wt. of ML=140.45 g Example-45

The mother liquor 140.45 gms obtained from above example-44 was equilibrated with KF (250 mg) at 60° C. for 5 hrs, cooled to room temperature and replenished with 11.23 g of diastereomer-A, and subjected for crystallization by cooling the solution from +20° to +9° in a suitable reactor as described in above example-40 following the same procedure and the solution was held at +9° C. for 20 hrs and filtered. The crystals were analyzed for SS-isomer content.
Wt. of solid=9.65 g
% Purity of crystals=96.5
Wt. of ML=144.04 gms Example-46

Preparation of Diastereomer-A 0.66 kg of Sodium cyanide and 6.24 kg of distilled water is charged simultaneously into a 20.0 lit. glass stirred reactor, equipped with a provision to cooling the reaction mass to −4° C., a mechanical stirrer, thermovel, dropping funnel and a vent tube. The contents are stirred well till a clear solution is obtained. 4.4 kg Dichloroethane, and 0.084 kg of tetrabutylammonium bromide (PTC) are charged in to the reactor under stirring, after which 1.75 kg of metaphenoxybenzaldehyde (MPBA) is added through a dropping funnel over a period of 25-30 mnts. at a temp. of 20-25° C. The reaction mixture is cooled to −3° to −5° C., 2.15 kg of (S)-fenvaleroyl-chloride is diluted with 2.2 kg of dichloroethane (DCE) and added over a period of 1½ to 2 hrs. through a dropping funnel maintaining the temperature between −3 to −4° C. under vigorous stirring. The temperature of reaction mass is maintained at this temperature for a further period of 2 hrs. The reaction is monitored by HPLC analysis (conversion of MPBA). The reaction mixture is brought to room temperature and the layers were allowed to separate out. The lower DCE layer is discharged weighed (11.19 kg) and kept aside. The upper aqueous layer (7.75 kg) containing sodium cyanide is discharged weighed and detoxified separately. The DCE layer (11.19 kg) is washed with (3×3.0 kg) distilled water, each time checking the pH of aqueous layer. The washings of DCE layer is continued till the pH of aqueous layer is neutral. The dilute DCE layer (11.19 kg) is taken for recovery of diastereomer-A.

The dilute DCE layer (11.19 kg) is weighed and fed into a Rotary evaporator equipped with a condenser provision for circulating cold water, vacuum system and a heater. The solvent DCE is removed at 40°-50° C. at 35-40 mm of Hg. After removing the last traces of DCE, nitrogen is purged into the system intermittently by applying vacuum to ensure the complete removal of solvent for a further period of 1 hr. The contents are cooled to room temperature, weighed (3.89 kg) and discharged into storage tank.
Wt. of diastereomer-A=3.89 kg
Ratio of SR:SS=45.2:43.5

Example-47

The material obtained from example 46 is used for preferential crystallization of esfenvalarate in an iterative manner as described below:

2.878 kg of Diastereomer-A (1:1 diastereomeric mixture) is charged into a crystallizer having provision for mechanical stirrer, thermovel, a calcium chloride guard tube and external cooling system. 8.684 kg of methanol is charged into the reactor to obtain about 25% solution and the contents are mixed well to obtain a homogeneous solution. The solution is initially cooled to 22° C. under stirring from room temperature, thereafter cooling is effected to 10° C. by decreasing the temperature at the rate of 4° C. per hour, at this temperature (10° C.) pure crystals of esfenvalerate (99.5%) is introduced into the system. Further cooling is effected carefully to reach the temperature (5-2° C.) at the rate of 1° C. per hour wherein the onset of crystallization is conspicuous. The solution is maintained around the onset of crystallization and the progress of crystallization is monitored by HPLC analysis wherein the concentration of SR-isomer in supernatant liquid is in the range of 55-60%. At this stage the solution is filtered off (ML-1) and the crystals obtained are weighed and air dried. This step is iterative and continued till esfenvalerate is obtained by crystallization process (5 cycles).
Wt. of crystals=0.516 kg
% Purity of crystals=96.5
Wt. of ML=10.67 kg

Example-47A

The filtrate enriched with SR-isomer ML-1 (10.67 kg) is charged into all glass jacketed stirred reactor provided with provision for temperature recording and heating system and the contents are heated to 62-65° C. for 5 hrs. The process of epimerization is monitored by HPLC analysis, drawing samples at regular intervals of time and the reaction is stopped when the sample showed a ratio of 1:1 with respect to SR:SS isomers. The solution is cooled to 30° C. and diastereomer-A (0.558 kg)equivalent to esfenvalerate obtained in earlier cycle is added and the solution is made up to 25% by adding methanol (0.424 kg). The process of crystallization is repeated by following the process of cooling from 30 to 3° C. as per the procedure described in example 47 for a period of 60 hrs. at the end of which the crystals obtained were separated weighed and dried
Wt. of crystals=0.432 kg
% Purity of crystals =97.2
Wt. of ML=10.887 kgs

Example-47B

The filtrate enriched with SR-isomer ML-2 (10.88 kg) obtained from example 47A is charged into all glass jacketed stirred reactor provided with provision for temperature recording and heating system and the contents are heated to 62-65° C. for 5 hrs. The process of epimerization is monitored by HPLC analysis, drawing samples at regular intervals of time and the reaction is stopped when the sample showed a ratio of 1:1 with respect to SR:SS isomers. The solution is cooled to 30° C. and diastereomer-A (0.452 kg) equivalent to esfenvalerate obtained in earlier cycle is added, solution is made up to 25% by adding methanol (0.504 kg). The process of crystallization is repeated by following the process of cooling from 24 to 1° C. as per the procedure described in example 47 for a period of 64 hrs. at the end of which the crystals obtained were separated weighed and dried.
Wt. of crystals=0.408 kg
% Purity of crystals=97.5
Wt. of ML=11.122 kgs

Example-47C

The filtrate enriched with SR-isomer ML-3 (11.12 kg) obtained from 47B is charged into all glass jacketed stirred reactor provided with provision for temperature recording and heating system and the contents are heated to 62-65° C. for 5½ hrs. The process of epimerization is monitored by HPLC analysis, drawing samples at regular intervals of time and the reaction is stopped when the sample showed a ratio of 1:1 with respect to SR:SS isomers. The solution is cooled to 30° C. and diastereomer-A (0.436 kg) equivalent to esfenvalerate obtained in earlier cycle is added, solution is made up to 25%. The process of crystallization is repeated by following the process of cooling from 26 to 1° C. as per the procedure described in example 47 for a period of 64 hrs. at the end of which the crystals obtained were separated weighed and dried.
Wt. of crystals=0.384 kg
% Purity of crystals=96.8
Wt. of ML=10.89 kgs

Example-47D

The filtrate enriched with SR-isomer ML-4 (10.89 kg) obtained from example 47C is charged into all glass jacketed stirred reactor provided with provision for temperature recording and heating system and the contents are heated to 62-65° C. for 5½ hrs. The process of epimerization is monitored by HPLC analysis, drawing samples at regular intervals of time and the reaction is stopped when the sample showed a ratio of 1:1 with respect to SR:SS isomers. The solution is cooled to 30° C. and diastereomer-A (0.398 kg) equivalent to esfenvalerate obtained in earlier cycle is added, solution is made up to 25%. The process of crystallization is repeated by following the process of cooling from 25 to −1° C. as per the procedure described in example 47 for a period of 65 hrs. at the end of which the crystals obtained were separated weighed and dried.
Wt. of crystals=0.184 kg
% Purity of crystals=92.4
Wt. of ML=10.826 kgs

Example-47E

The filtrate enriched with SR-isomer ML-5 (10.826 kg) obtained from example 47D is charged into all glass jacketed stirred reactor provided with provision for temperature recording and heating system and the contents are heated to 62-65° C. for 6½ hrs. The process of epimerization is monitored by HPLC analysis, drawing samples at regular intervals of time and the reaction is stopped when the sample showed a ratio of 1:1 with respect to SR:SS isomers. The solution is cooled to 30° C. and diastereomer-A (0.280 kg) equivalent to esfenvalerate obtained in earlier cycle is added, solution is made up to 25%. The process of crystallization is repeated by following the process of cooling from 29 to −5° C. as per the procedure described in example 47 for a period of 75 hrs. at the end of which the crystals obtained were separated weighed and dried.

Wt. of crystals=0.256 kg
% Purity of crystals=94.5
Wt. of ML=10.520 kgs

TABLE

| Expt. No. | Wt. of Crystals (SS Isomer) | % purity |
|---|---|---|
| 47 | 0.516 | 96.5 |
| 47A | 0.432 | 97.2 |
| 47B | 0.408 | 97.5 |
| 47C | 0.384 | 96.8 |
| 47D | 0.184 | 92.4 |
| 47E | 0.256 | 95.4 |

The Main Advantages of the of the Present Invention Are:

1. The present invention makes it possible to obtain high optically pure (>95%) SS isomer in an iterative manner
2. The another advantage of the invention is the effective use of the unwanted SR isomer from the ML by epimerisation process using catalyst and recycling the same iteratively as such
3. Another advantage is consecutively using thus equilibrated ML of one cycle in another cycle as such avoids many process steps. Replenishing the ML with fresh diastereomer-A to the extent of crystals of SS isomer obtained maintains the saturated state of the solution.
4. Yet another advantage is the catalyst used for epimerisation is reused without isolation for further batches.
5. Yet another advantage is that the method effectively combines the enrichment and crystallization process without isolation of the catalyst and thereof all the desired isomer (SS isomer) can be effectively obtained from diastereomer-A.

TABLE 1

| Expt. No. | Wt. of dia-A (gms) | % solution w/w | Solvent system | Seeding Temp. (° C.) | Temp. profile (° C.) | Time hrs. | Wt. of crystals (gms) | % Purity of crystals (SS) | Remarks |
|---|---|---|---|---|---|---|---|---|---|
| KR-1 | 6.78 | 31.5 | MeOH | No seed crystals | −6 | 47 | No crystals | — | The R.M. warmed to 41° turbid solution at R.T. two layers; TEA 3 ml |
| KR-Ia | 6.78 | 33 | MeOH | — | 23 to −3 | 19 | Crystals dissolved | 40.37 | At −2° C. solid lump formed. Solution became white turbid |
| KR-2 | 5.01 | 50 | Ethanol | 5 | 5-0 | 90 | 0.5 | 43.14 | Crystallization started after 24 hrs |
| KR-3 | 4.98 | 21.4 | Hexane | +5 | 21 to −5 | 52 | 3.44 | 41.39 | TPP added 71 mg 2 mole % |
| KR-4 | 10.04 | 33 | MeOH | +5 | 10 | 24 | — | — | No preferential crystallisation |
| KR-5 | 10.00 | 33 | MeOH | +5 | — | — | — | — | No data |
| KR-6 | 10.0 | 33.18 | Heptane Toluene/ MeOH | −13 | 25 to −16 | 65 | No crystals Viscous mass | 44.1 | Added 7 gr of dry MeOH |
| KR-7 | 12.39 | 33 | MeOH | −22 | 24 to −22 | 163 | No crystals | — | — |
| KR-8 | 5.0 | 30 | Isopropanol | −12 | 5 to −12 | 102 | No crystals | — | Precipitate formed |
| KR-9 | 9.84 | 35.6 | MeOH | — | +15 | 18 | 8.86 | 46.57 | Refluxed for 1 hr at 65° C. |
| KR-9a | 1.31 | −8.03 | MeOH | 2 | 5 to −15.6 | 22 | 0.51 | 95 | Crystals at −15° C. ML of KR-9 |
| KR-10 | 10.01 | 33 | MeOH | −5 | 5 to −15.6 | 95 | 2.10 | 45.4 | Refluxed for 1 hr at 65° C. |
| KR-10a | 7.9 | 35 | MeOH | −15 | −15 | 90 | 3.57 | 51.27 | ML of KR-10 |
| KR-11 | 26.23 | 7 | MeOH | 14 | 14 to −16 | 40 | 18.00 | 51.4 | |
| KR-12 | 9.2 | 7 | MeOH | −13 | +5 to −16 | 114 | 0.5 | 47.7 | ML of Kr-9 + ML of KR-11, concentrated to get 7% solution |
| KR-13 | 8.82 | 33 | MeOH | −10 | 20 to −5 | 20 | 4.75 | 48.17 | Crystals of KR-11 dissolved, refluxed for 1 hr at 67° C. |
| KR-14 | 4.1 | 20 | MeOH | −15 | 15 | 92 | 1.2 | 46.17 | ML of KR-13 |
| KR-15 | 10.94 | 33 | MeOH | −13 | 5 to −17 | 140 | 0.26 | 92 | Crystals washed with cold hexane |
| KR-16 | 11.74 | 33 | MeOH | 5 | 5 to −1 | 35 | 9.40 | 47.59 | Crystals of KR-14, 10, 12, 11 melted and dissolved in MeOH. |
| KR-17 | 2.3 | 12 | MeOH | −18 | −17 to −18 | 76 | 1.75 | 48 | ML of KR-16 |
| KR-18 | 53.91 | 33.8 | MeOH | 10 | 22 to −8 | 24 | 23.87 | 48.01 | Refluxed for 1 hr; at 8° C. crystals observed |
| KR-19 | 30.04 | 27.8 | MeOH | −14 | 5 to −15 | 67 | 1.07 | 90 | ML of KR-18 |
| KR-19A | 29 | 30 | MeOH | −15 | −15 | 66 | 8.05 | 48.28 | ML of KR-19 |

TABLE 1-continued

| Expt. No. | Wt. of dia (gms) | % solution (w/w) | Solvent system | Seedling Temp. (° C.) | Temp. profile (° C.) | Time (hrs.) | Wt. of Crystals (in gms) | % Purity of crystals (SS) | Remarks |
|---|---|---|---|---|---|---|---|---|---|
| KR-20 | 10.01 | 25 | MeOH/Heptane/Toluene | −10 | RT to −16 | 138 | 3.29 | 95.32 | 0.9 ml MeOH/Ammonia KR-6 |
| KR-21 | 10.06 | 33 | Heptane Toluene/MeOH | −15 | 5 to −16 | 48 | 8.65 | 47.32 | 0.9 ml MeOH/NH₃ crystal of KR-9, 10 |
| KR-22 | 52.82 | 32.18 | MeOH | −14 | −14 | 170 | 20.0 | 47.5 | Refluxed dia-A for 1 hr at 65° C. |
| KR-23 | 11.16 | 30 | MeOH/Toluene/Heptane | 14 | 23 to −14 | 240 | 0.43 | 97.39 | KR-22 ML compound |
| KR-24 | 10.85 | 32.6 | MeOH/Toluene/Heptane | −14 | −15 | 144 | 0.9 | 98 | KR-22 ML compound |

| Expt. No. | Wt. of dia (gms) | % solution (w/w) | Solvent system | Seedling Temp. (° C.) | Temp. profile (° C.) | Time (hrs.) | Wt. of Crystals (in gms) | % Purity of crystals (SS) | Remarks |
|---|---|---|---|---|---|---|---|---|---|
| KR-25 | 21.14 | 33 | Heptane/Toluene/MeOH | −15 | −15 | 280 | Gummy material | 83.91 | Crystal of KR-22 |
| KR-26 | 10.11 | 40 | Heptane/Toluene/MeOH | −15 | −15 | 24 | No crystals | — | KR-18 crystals, No preferential of crystallization |
| KR-27 | 2.46 | 30 | Heptane/Toluene | — | — | — | 1.5 | 99 | Recrystallizaion of pure material |
| KR-28 | 4.18 | 14 | Heptane/Toluene | 10 | 25 to 10 | 24 | 0.73 | 98.28 | Recrystallization |
| KR-28C | 3.31 | 24 | Heptane/Toluene | RT | — | 24 | 1.03 | 97.55 | ML of KR-28 |
| KR-29 | 20.0 | 24.6 | MeOH | −15 | −15 | 72 | 9.22 | 45 | KR-16 + KR-18 material |
| KR-30 | 10.0 | 11.46 | MeOH | −11 | −15 to 18 | 96 | 6.80 | 57 | ML of KR-29; 0.0724 gms of seed 99.3% added |
| KR-31 | 40.0 | 33 | Heptane/Toluene/MeOH | −50 | 0 | 22 | 28.41 | 42 | Refrigerator temp. KR-27 crystals as seed (99.31) and NH₃. then −15° C. for 5 hrs material filtered |
| KR-32 | 9.0 | 14.8 | MeOH | 0 | −10 | 48 | 9.0 | 41 | 1 ml ammonia; pure seed 99.3% was added |
| KR-33 | 22.5 | 12 | MeOH | 5 | −15 | 96 | 10.89 | 39.3 | No base was added; large seed crystals were added, KR-29, 31 material |
| KR-34 | 6.8 | 42.2 | Heptane/Toluene | 0 | 0-7° | 24 | 3 | 49 | Solids of KR-30 |

| Expt. No. | Wt. of dia-A (gms) | solvent system | % solution (w/w) | Wt. of crystals (SS) (gms) | % Purity of crystals | Time of Reaction (hrs) | Temp. Profile (° C.) | Seeding Temp. (° C.) | Base | Remarks |
|---|---|---|---|---|---|---|---|---|---|---|
| KR-35 | 152.57 (ML) | MeOH | ≈7.6 | — | — | — | — | — | 1.0 ml NH₃/MeOH | No data |
| KR-36A | 20.0 | MeOH | 12.34 | 5.6 | 93.2 | 87 | −7 to −14 | −11 | 4.0 ml NH₃/MeOH | 23% yield ML of KR, 31, 32, 33, 34 without stirring |
| KR-36B | 20.0 | MeOH | 12 | 7.0 g | 97.4 | 87 | 4 to −8 | −4 | 4.0 ml NH₃/MeOH | 35% yield with stirring ML of KR-31, 32, 33, 34 |
| KR-37 | 27.91 | MeOH | 12 | 0.03 | 86 | 140 | −15 | −15 | 9.0 ml NH₃/MeOH | ML of KR 36A + 36B. Crystals observed were at low temp. dissolved at ≈RT |
| KR-38 | 16.07 | MeOH | 12 | 8.86 | 43.2 | 94 | 0 to −5 | 0 | 3.2 ml, NH₃/MeOH | KR-30, 34, 33 solids |
| KR-39 | 7.36 | MeOH | 11.88 | 2.95 | 98.46 | 42 | −6 to −15 | −8 | 2.0 ml NH₃/MeOH | 39% ≈38 hrs. ML of KR-38 |
| KR-40 | 143 | MeOH | 25 | 116.9 | 41.0 | 18 | −18 | 1.25 | 11.17 NH₃/MeOH | SAF-18 material |
| KR-41 | 26.4 | MeOH | 6.36% | ≈2.0 g | 35% | 68 hrs | −18 | 0.22 g of 99.7% at −15 | NH₃/MeOH | ML of KR-40 |

| Expt. No. | Wt. of Dia-A (in gms) | solvent system | % solution (w/w) | Wt. of crystals (SS) | % Purity of crystals (SS) | Time of Reaction (hrs) | Temp. ° Profile (° C.) | Seeding Temp. (° C.) | Base | Remarks |
|---|---|---|---|---|---|---|---|---|---|---|
| KR-42 | 24.81 | MeOH | 12 | 3.28 | 99.4 | 184 | −7 to −17 | Seed crystal | 2 ml | ML of KR-41 |

TABLE 1-continued

| Expt. No. | Wt. of dia-A (gms) | solvent system | % solution (w/w) | Wt. of crystals (SS) (gms) | % Purity of crystals (SS) | Time of Reaction (hrs) | Temp. Profile (° C.) | Seeding Temp. (° C.) | Base | Remarks |
|---|---|---|---|---|---|---|---|---|---|---|
| 42-A | 21.6 | MeOH | 35 | 77.97 | 31.4 | 45 | −2 to −10 | 99.7 (LC) at −14° C. Pure crystal at −15° C. | 4 ml NH₃/MeOH | ML of KR-42 solids, dissolved conc. to give 17.97 g KR-47 |
| KR-43 | 40.0 g | MeOH | 12 | 13.56 | 37.12 | ≈24 | −8 | 99.7 at −5 | — | @-8.5° after 2 hrs. crystallization started. SM SAF-18 |
| KR-43A | 26.5 | MeOH | 8.75 | — | — | 220 | −14 to −18 | Seed crystal 99.7 at −14 | — | 3 days at −15 kept in fridge for one day; SM is ML-KR-43. No crystals |
| KR-44 | 56.66 g | MeOH | 33 | 45.46 | 43.58 | 23 | 0 to −2 | 0 | — | SAF-18 solids |
| KR-44A | 11.10 | MeOH | 12 | 1.77 g | 97 | 49 | −4 to −12 | −4 | 4.5 ml NH₃/MeOH | ML of KR-44 seed crystals one scoop (99.7%) |

| Expt. No. | Wt. of dia-A (gms) | solvent system | % solution (w/w) | Wt. of crystals (SS) (gms) | % Purity of crystals (SS) | Time of Reaction (hrs) | Temp. Profile (° C.) | Seeding Temp. (° C.) | Base | Remarks |
|---|---|---|---|---|---|---|---|---|---|---|
| KR-45 | 20.0 g | MeOH | 6 | 1.52 | 40.45 | 53 | −10 to 17° | 4 scoops (99.7%)@ −15° C. | 4.5 ml NH₃/MeOH | Few crystals before adding NH₃ and seed kept at −15° C. for 17 hrs (.44 g crystals obtained decanted. Then base/seed added with 5 hrs crystals of 1:1 only |
| KR-46 | 10.0 g | IPA | 19.8 | — | — | 50 | 15 to 10 | 13 | 3.5 ml NH₃/MeOH | KR-44 solid; no crystals were obtained |
| KR-47 | 27.94 | MeOH | 32.72 | — | — | 63 | −18 | −14 | 2.5 ml NH₃/MeOH | To the ML of KR-42A 10 gms. Of KR 45 solid added; no crystals |
| KR-48 | 26.21 | MeOH | 35.7 | — | — | 142 | 7 to −9 | −17 | 2.5 ml NH₃/MeOH | ML of KR-43A; ML gone bad; no crystals |
| KR-49 | 25.18 g | Heptane Toluene MeOH | 33 | — | — | 76 | RT to −18 | −18 | 3 ml NH₃/MeOH | KR-44 solid; no crystals clear solution |
| KR-50 | 10.0 g | MeOH | 33 | — | — | 120 hrs | 25 to 17 | — | — | KR-32, 33 solids Expt. To find the appearance of turbidity |
| KR-51 | 5.02 | MeOH/H₂O | 33 | Gummy layer | 40.05 | 110 | 25 to −10 | — | — | Gummy bottom layer |

| Expt. No. | Wt. of dia-A (gms) | % solution (w/w) | solvent system | Seeding temp (° C.) | Temp. Profile (° C.) | Time of Reaction (hrs) | Wt. of crystals SS (gms) | % Purity of crystals (SS) | Base | Remarks |
|---|---|---|---|---|---|---|---|---|---|---|
| KR-52A | 3.04 | 35 | MeOH, H₂O | 15 | 15 | 23 | 4.84 | 43.87 | Methanolic ammonia | Mixed together and filtered; ML concentrated; Wt. 2.97 gms |
| KR-53 | 3.01 | 33 | MeOH, H₂O | 15 | 15 | 27 | 4.84 | 43.87 | Methanolic ammonia | |
| KR-54 | 2.057 | 33 | MeOH, H₂O | 15 | 15 | 27 | 1.9 | 43.87 | Methanolic ammonia | |
| KR-55 | 79.53 | 35 | Heptane, toluene, methanol | −15 | 23 to −19 | 120 | 17.4 | 38.28 | MeOH/NH₃ 5 ml | |
| KR-56 | 9.94 | 33 | Methanol | −10 | 35 to −19 | 36 | — | 48.68 | Ammonium acetate 0.054 gms | Solid of KR-50 |
| KR-57 | 56.47 | 33 | Heptane, methanol toluene | −13 | 16 to −18 | 67 | 2.48 | 35.38 | Methanolic ammonia 6 ml | — |
| KR-58 | 53.99 | 34 | Heptane, methanol, toluene | −14 to −18 | −12 to −18 | 95 | — | — | — | ML of KR-57; no crystals |
| KR-59 | 6.62 | 30 | Heptane, methanol, toluene | −18 | RT to −18 | 50 | — | — | 2 ml of Methanolic ammonia | KR-43 solid; no crystals |

| Expt. No. | BASE | Wt. of diaA (gms) | % solution (w/w) | Wt. of crystals (gms.) | % purity of crystals (SS) | Time (hrs) | Temp. Profile (° C.) | Remarks |
|---|---|---|---|---|---|---|---|---|
| KR-60 | S(−) α-methylbenzyl Amine 0.9 g ≈2 mol % | 6.27 | 12 | — | 40.9 | 42 | −5 to −15 | Seed crystal at −5° C.; solvent MeOH |

TABLE 1-continued

| Expt. No. | BASE | Wt. of dia A (gms) | % solution (w/w) in IPA | Wt. of crystals (gms.) | % purity of crystals (SS) | Time (hrs) | Temp. Profile (° C.) | Remarks |
|---|---|---|---|---|---|---|---|---|
| KR-61 | T.B.A.B. (0.12 g) | 5.56 | 12 | 6.90 | 43.9 | 42 | −5 to −15 | — |
| KR-62 | R(+) α-methylbenzyl amine 0.08 g ≈2 mol % | 5.33 | 12 | 2.87 | 52.5 | 160 | −5 to −15 | Seed crystals at −5° C.; more solids but changed |
| KR-63 | TBAOH 0.08 gms ≈2 mol % | 6.22 | 12 | 3.38 | 51.24 | 165 | −5 to −15 | Seed crystal at6 −5° C. |
| KR-64 | 2-2-OCH$_3$ ethoxyethylamine, 2 mol % 0.07 gms | 4.02 | 12 | 0.72 | 43.3 | 75 | −5 to −15 | |
| KR-65 | Quinoline 2 mol % 0.08 gms | 4.62 | 12 | 0.46 | 43.2 | 167 | −5 to −15 | Seed crystals at −5° C. MeOH |
| KR-66 | NNDMA 2 mol % 0.05 gms | 5.51 | 12 | 0.45 | 42.8 | 137 | −5 to −15 | Seed crystals at −5° C. MeOH |
| KR-67 | TBASO$_4$ 2 mol % 0.12 gms | 6.53 | 12 | 3.2 | 44.02 | 137 | −5 to −15 | Seed crystals at −5° C. MeOH |
| KR-68 | R(+)Amine 2 mol %, 0.03 | 5.16 | 12 | 2.48 | 48.46 | 115 | −5 to −20 | MeOH; seed crystals at −5° C. |
| KR-69 | TBAOH 2 mol % 0.06 gms | 5.14 | 12 | 0.81 | 96.38 | 115 | −5 −17 | MeOH; seed crystals at −5° C. |

| Expt. No. | BASE | Wt. of dia A (gms) | % solution (w/w) in IPA | Wt. of crystals (gms.) | % purity of crystals (SS) | Time (hrs) | Temp. Profile (° C.) | Remarks |
|---|---|---|---|---|---|---|---|---|
| KR-70 | R + Amine | 5.20 | 12 | — | — | 140 | −5 to −19 | Gummy to the bottom. At RT two layers. seed crystals at −5° C. |
| KR-71 | TBAOH | 5.15 | 12 | — | — | 140 | | Gummy to the bottom; at −5° C. at two layers conc.; seed crystals at −5° C. |

| Expt. No. | Wt. of dia-A (gms) | solvent system | % solution (w/w) | Wt. of crystals (SS) (in gms) | % Purity of crystals (SS) | Time of Reaction (hrs) | Temp. Profile (° C.) | Seeding Temp. (° C.) | Base | Remarks |
|---|---|---|---|---|---|---|---|---|---|---|
| KR-72 | 5.7 | toluene | 12 | No crystals | — | 160 hrs | 6 to −20 | −3.5 | TBAOH | No crystals, seed crystal as it contain TBAOH from previous expt. |
| KR-73 | 20.9 | MeOH | 12 | No crystals | — | 140 hrs | −5 to −20 | −5 | 2.9 g TBAOH | SAF-20 material reaction material decomposed |
| KR-74 | 5.22 | MeOH | 12 | No crystals | — | 140 hrs | +5 to −20 | −3 | DBN 2 mol % 0.08 g | Material decomposed |
| KR-75 | 9.79 | MeOH | 12 | Crystal 1:1 at RT dissolved | 41.49 | 140 hrs | 5 to −2 | −3.5 | TEA 9 mol % 0.2 g | At RT after 24 hrs crystal dissolved composition ≈1:1 NMR shows decomposition |
| KR-76 | 5.22 | toluene | 33 | No crystals | — | 142 hrs | −5 to −20° C. | −15 | NH$_3$/MeOH 1 ml | Added IPA after 120 hrs |
| KR-77 | 4.99 | Heptane:toluene 73:26 | 29.4 | 2 layers | — | 168 | −5 to −20 | −5 | 0.5 ml, 6% MeOH/NH$_3$ | |
| KR-78 | 5.02 | Toluene + isopropanol 32 + 67 | 27.8 | 2 layers | — | 168 | −5 to −20 | −5 | 0.5 ml, 6% MeOH/NH$_3$ | Stepwise cooling −5 |
| KR-79 | 5.06 | Heptane Ethylacetate Toluene in the ratio 74:10:15 | 29.8 | 2 layers | Two layers | 164 | −5 to 10 | −5 | 0.5 ml, 6% MeOH/NH$_3$ | Stepwise cooling |

| Expt. No. | BASE | Wt. of dia A (gms) | % solution (w/w) | Solvent system | Wt. of crystals (SS) (gms) | % purity of crystals (SS) | Time (hrs) | Temp. profile (° C.) | Remarks |
|---|---|---|---|---|---|---|---|---|---|
| KR-80 | 4 ml of MeOH/NH$_3$ 6% | 20.02 | 33.25 | MeOH | No crystals | — | 17 | 7 to −5 | Julobo failure at 33° C. over high conc. gave for NMR aldehyde is present. Seed crystal at 7° C. |
| KR-81 | 1.0 ml NH$_3$/MeOH | 4.99 | 12.15 | MeOH | 0.33 | 89 | 120 | −5 to −19 | Stepwise cooling very few crystal indicating transformation kept |

TABLE 1-continued

| Expt. No. | BASE | Wt. of dia A (gms) | % solution (w/w) | Solvent system | Wt. of crystals (SS) (gms) | % purity of crystals (SS) | Time (hrs) | Temp. profile (° C.) | Remarks |
|---|---|---|---|---|---|---|---|---|---|
| KR-82 | 4.0 ml of 6% NH₃/MeOH | 20.02 | 33.00 | MeOH | 9.94 | 41 | 96 | −5 to −19 | under stirring for 6 days; seed crystals at −5° C. Stepwise cooling hard mass filtered; seed crystals at −5° C. |
| KR-83 | 2.0 ml of 6% NH₃ | 8.89 | 11.94 | MeOH | 1.7 | 97.2 | ≈40 | −18 to −20 | Seed crystal at −18° C.; ML of KR-82 |
| Kr-84 | 2.0 ml NH₃/MeOH | 5.0 | 12.0 | MeOH | .75 | 57.89 | 60 | −15 for 3 days −18 for 24 hr | Curdy not settling filtered seed crystals at −15° C. |
| KR-85 | 2.0 ml MeOH/NH₃ | 5.03 | 17.4 | MeOH | 1.28 | 92.9 | 91 | −15 to −18 | Expt. without stirring; seed crystal at −15° C. |
| KR-86 | 2.0 ml of 6% NH₃/MeOH | 5.05 | 17.66 | MeOH | 2.18 | 40.0 | 22 | −15 | Expt. Without stirring; seed crystal at −15° C. |

| Expt. No. | BASE | Wt. of dia A (gms) | % solution (w/w) | Solvent system | Wt. of crystals (SS) (gms) | % purity of crystals (SS) | Time (hrs) | Temp. profile (° C.) | Remarks |
|---|---|---|---|---|---|---|---|---|---|
| KR-87 | 2 ml of 6% NH₃/MeOH | 8.0 | 16.82 | MeOH | 5.61 | 40.8 | 50 | 5 to −15 | Was used after mixing ML of 88+ see expt KR-87 dt. 2.7.97; seed crystal at 5° C.; added 0.5 ml glacial CH₃COOH |
| KR-88 | 2.0 ml of 6% NH₃/MeOH | 5.05 | 12.02 | MeOH | 0.84 | 89.92 | 120 | −5 to −15 | Mixed with KR-87 Ml; Expt. Without stirring; seed crystals at −15° C. |
| KR-89 | 2.0 | | 18.11 | MeOH | 2.34 | 44.06 | 72 | −15 | Expt. Without stirring; seed crystals at −15° C. |
| KR-90 | 2.0 ml NH₃/MeOH 6% | 9.61 | 21.02 | MeOH | 0.08 | — | 52 | −10 to −15 | Changed to stirring on 9.7.97; ML KR 88 + 89 87; seed crystals at −15° C. |
| KR-91 | 2.0 ml NH₃/MeOH 6% w/w | 5.05 | 18.1 | MeOH | 2.65 | 38.99 | 24 | −15 | Std at 156.00 hrs at 18.0 maximum than usually seen; seed crystals at −15° C. |
| KR-92 | 10 ml NH₃/MeOH | 20.75 | 18.09 | MeOH | 2.43 | 94.5 | 112 | −8 | Inj of ML repeated as pure sample 94% crystals contamination suspected; solid of KR 76 – 79; seed crystal at −10° C.; ML = 116.08 gms |
| KR-93 | 10 ml NH₃/MeOH 6% | 23.25g | 19.26 | MeOH | 1.16 | 97.6 | 48 | −8.6 | 2 ml of ACOH was added; seed crystals at −8° C.; ML of KR-92 + 5.0 g of liq. Dia-A used in this expt. |
| KR-93A | 9 ml NH₃/MeOH 6% | 22.09 | 17.05 | MeOH | No crystals | — | 80 | −8.6 | No crystal conc. to 33% spoiled while concentrating; seed crystal at −8° C. |

| Expt. No. | Wt. of dia-A | % solution (w/w) | Solvent system | Seeding Temp. (° C.) | Temp. profile (° C.) | Time (hrs) | Wt. of crystals (SS) (gms) | % Purity of crystals (SS) | BASE | Remarks |
|---|---|---|---|---|---|---|---|---|---|---|
| KR-94 | 4.96 | 30 | MeOH | 10 | 10 | 24 | 4.83 | 42.8 | — | KR-82, 91, 68 solids. Seed crystal present |
| KR-95 | 4.98 | 21% | MeOH | 10 | 10 | 24 | 2.78 | 38.2 | — | KR-82, 88, 91, 87 solids. Seed crystal present |
| KR-96 | 4.7 | 10.38 | MeOH | 10 | 10–0 | 113 | 2.9 | 38 | — | KR-82, 68, 91, 87 solids. Crystal present at 5° C. |
| KR-97 | 5.01 | 15.7 | MeOH | 10 | 10 | 24 | 2.2 | 37.8 | — | KR-82, 68, 91, 87 solids |
| KR-98 | 5.08 | 25 | MeOH | 10 | 10 | 24 | 1.34 | — | — | SAF-21 material |
| KR-99 | 4.99 | 20 | MeOH | 10 | 10 | 24 | 1.47 | 38 | — | SAF-21 material |
| KR-100 | 5.00 | 10 | MeOH | 5 | 10 to −5 | 50 | 1.08 | 39.25 | — | SAF-21 material |
| KR-101 | 4.99 | 15 | MeOH | 10 | 10 | 24 | 0.8 | 42.94 | — | SAF-21 material |
| KR-102 | 4.94 | 10 | MeOH | 7 | 8 to −8 | 120 | 1.30 | 36.68 | 2 ml NH₃/MeOH | SAF-21 material |
| KR-103 | 4.95 | 10 | MeOH | 7 | 8 to −2 | 46 | 1.13 | 41.01 | — | SAF-21 material |
| KR-104 | 4.19 | 13.7 | MeOH | 8 | 8 to −12 | 46 | 1.13 | 42.81 | — | ML of KR-101 |
| KR-105 | 18.64 | 12 | MeOH | −8 | 0 to −18 | 138 | 3.76 | 72.2 | 8 ml NH₃/MeOH | KR-91, 98, 99, 100, 103, 104 MLs, |
| KR-106 | 5 | 25 | Heptane/toluene | 28 | 10 | 88 | 1.98 | 42.88 | — | KR-60, 61 solids |
| KR-107 | 13.5 | 32 | MeOH | 0 | 0 to −10 | 138 | No crystals | — | 2 ml NH₃/MeOH | ML of KR-105; neutralized with ACOH concentrated |

TABLE 1-continued

| KR-108 | 39.39 | 33 | MeOH | 5 | 5 to −15 | 240 | No crystals | — | 10 ml of NH$_3$/MeOH | ML of KR-107 + KR 55, 94 – 97 solids. |
| KR-109 | 12.12 | 35.11 | MeOH | 25 | 25 to 10 | 18 | — | — | | 0.13 MPBA added; solid Aα(1:1) Restd. As 109A |

| Expt. No. | Wt. of dia-A | % solution (w/w) | Solvent system | Seeding Temp. (°C.) | Temp. profile (°C.) | Time (hrs) | Wt. of crystals (SS) (gms) | % Purity of crystals (SS) | Remarks |
|---|---|---|---|---|---|---|---|---|---|
| KR-109A | 12.11 | 33 | MeOH | 10 | 10 | 27 | — | 47.2 | ML of KR-109; a crystal tested and made uniform solution 50 μl MPBA added |
| KR-109B | 12.11 | 33 | MeOH | 10 | 10 | 20 | — | 47.2 | ML of KR-109A; a crystal tested and made uniform solution 150 μl MPBA added |
| KR-109C | 12.11 | 33 | MeOH | 10 | 10 | 40 | — | — | ML of KR-109B |
| KR-110 | 12.11 | 33 | MeOH | −15 | 10 to −15 | 75 | No crystals | — | ML of KR-109C, 1 ml NH$_3$/MeOH 2 ml of KR-108 mixed with KR-109C |
| KR-111 | 32.22 | 12 | MeOH | −5 | −5 to −15 | 120 | 3.70 | 96.5 | ML of KR-65, 66, 67, 95, 96, 97, 5 ml NH$_3$/MeOH |
| KR-112 | 19.89 | 12 | MeOH | −5 | −5 to −15 | 260 | No crystals | — | 3 ml NH$_3$/MeOH mixed M.L's taken for experiment after concentration. |
| KR-113 | 7.88 | 12 | MeOH | −5 | −5 to −15 | 118 | No crystals | — | Mixed M.L's; 2 ml NH$_3$/MeOH |
| KR-114 | 5.31 | 27.4 | Heptane/toluene | 10 | 10 | 66 | 2.84 | 97.19 | Old samples of KR-36, two layers |
| KR-115 | 3.05 | 12.03 | MeOH | −15 | −15 | 114 | 1.05 | 43.25 | KR-111 solid melted. 2 ml NH$_3$/MeOH |
| KR-116 | 38.15 | 12 | MeOH | +5 | 5 to −14 | 92 | 1.2 | 44.2 | SAF-22 material, 16 ml NH$_3$/MeOH |

| Expt. No. | Wt. of dia-A (gms) | % solution (w/w) | Solvent system | Seeding Temp. (°C.) | Temp. profile (°C.) | Time (hrs) | Wt. of crystals (SS) (gms) | % Purity of crystals (SS) | Remarks |
|---|---|---|---|---|---|---|---|---|---|
| KR-117 | 37.92 | 33 | MeOH | 1 | 19 to −14 | 110 | No crystals | — | SAF-22 + KR116; 16 ml NH$_3$/MeOH |
| KR-118 | 32.18 | 33 | MeOH | −14 | 8 to −14 | 94 | 14.0 | 43.5 | SAF-24, 12 ml N$_3$/MeOH |
| KR-119 | 18 | 21.4 | MeOH | −14 | −14 | 140 | No crystals | — | ML of KR-118, 65 ml NH$_3$/MeOH |
| KR-120 | 9 | 33 | TEA | −14 | −14 | 140 | — | — | No crystals |
| KR-121 | 155 | 32 | MeOH | −5 | −14 | 112 | 92.86 | 46.84 | SAF-27 |
| KR-122 | 63 | 20 | MeOH | −14 | −14 | 46 | 33.8 | 48.24 | ML of KR-121 |
| KR-123 | 188 | 33 | MeOH | 10 | 10 | 280 | 159 | 46.58 | SAF-27 material |
| KR-124 | 334 | 33 | MeOH | −14 | −14 | 285 | 270.9 | 48.25 | Pilot plant batch |
| KR-125 | 220 | 33 | MeOH | 10 | 10 | 80 | 140.8 | 47.8 | No data, SAF-28, Pilot plant batch |
| KR-126 | 124 | 30 | MeOH | −6 | 0 to −14 | 168 | 202.0 | 42.6 | MLs of KR-122 to 124 |
| KR-127 | 18.17 | 12 | MeOH | 10 | 10 to −14 | 66 | 6.61 | 44.1 | ML of KR-125 |
| KR-128 | 11.56 | 8 | MeOH | 0 | 0 to −14 | 202 | No crystals | — | ML of 127 |
| KR-129 | 10.10 | 33 | IPA | 10 | 10 to −17 | 20 | No crystals | — | KR-125 solid |
| KR-130 | 1152 | 36 | MeOH | −5 | −5 | — | 651.63 | 42.4 | |
| KR-131 | 10.04 | 22.84 | Isobutanol toluene | 0 | 5 to −5 | 167 | No crystals | — | KR-124 solids |
| KR-132 | 7.06 | 33 | T.Butanol TEA | 1 | −1 | 90 | — | — | KR-124 solids. At RT crystals dissolved |
| KR-132A | 9.98 | 15.2 | Heptane TEA | 4 | 2 to −10 | 138 | — | — | KR-124 solids; A crystal sowed 40.6%; very few crystals not sep. |

| Expt. No. | Wt. of dia-A | % solution (w/w) | Solvent system | S'eeding Temp. (°C.) | Temp. profile (°C.) | Time (in hrs) | Wt. of crystals (SS) | % Purity of crystals (SS) | Remarks |
|---|---|---|---|---|---|---|---|---|---|
| KR-133 | 9.98 | 20 | Heptane TEA | −10 | −10 | 95 | No crystals | — | KR-132 A ML |
| KR-134 | 5.08 | 33 | Heptane TEA | −11 | −11 | 80 | — | 40.6 | A cryst showed enricment, during sampling process more crystals appeared (1:1) |
| KR-135 | 5 | 32 | Heptane TEA | −5 | −5 | 90 | 0.15 | 86.8 | |
| KR-135A | 4.85 | 33 | Heptane TEA | −5 | −4 to −13 | 240 | 2.57 | 44 | ML of KR-135 |

TABLE 1-continued

| Expt. No. | Wt. of dia-A (gms) | % solution (w/w) | Solvent system | Seeding Temp. (° C.) | Temp. profile (° C.) | Time (hrs) | Wt. of crystals (SS) (gms) | % Purity of crystals (SS) | Remarks |
|---|---|---|---|---|---|---|---|---|---|
| KR-136 | 8 | 40 | Heptane TEA | −5 | −5 | 90 | 0.11 | 77.2 | |
| KR-136A | 7.89 | 40 | Heptane TEA | −5 | −5 to −13 | 240 | 2.85 | 54 | ML of KR-136 |
| KR-137 | 120 | 40 | Heptane TEA | −4 | −4 | 144 | 34.0 | 40.9 | KR-124 crystals |
| KR-138 | 100 | 40 | Heptane TEA | −6 | 0 to −6 | 163 | 27.10 | 43.2 | Hep:TEA 1:1, crystals of KR-124 |
| KR-139 | 80 | 33 | Heptane TEA | 4 | 4 | 72 | No crystals | — | ML of KR-137 |
| KR-140 | 5.04 | 24 | Heptane I.P.amine | 4 | 4 | 168 | 0.85 | 28.2 | more decomposed products |
| KR-141 | 4.0 | 4.0 | Heptane (S)-α-methyl benzylamine | 4 | 4 to −5 | 192 | No crystals | — | Layer separation observed |
| KR-142 | 12.05 | 39 | TEA, Toluene, Heptane | −1 | 2 to −1 | 63 | No crystals | — | Tol:TEA:Hep = 1:2:3 ratio |
| KR-143 | 12.05 | 40 | TEA, Hexane | −1 | 2 to −3 | 63 | 3.25 | 45.6 | |
| KR-144 | 5.0 | 20 | MeOH | 4 | 4 | 96 | 1.0 | 51.27 | Isopropylamine 100 µl added |
| KR-145 | 4.01 | 56 | Diisopropylamine | 4 | 4 | 120 | No crystals | — | Clear solution. No crystals |
| KR-146 | 40.21 | 32.8 | Heptane Toluene MeOH | 4 | 4 | 24 | No crystals | — | M:He:T (28:47:65) KR-130 compound two layers separated |
| KR-147 | 1.5278 | 10 | MeOH | −1.9 | 0 to −5 | 280 | 0.5 | 98 | Two layers separated No data, seed crystals Wt. 0.37/gr. |
| KR-147A | 1.0 | 16 | MeOH | −10 | −10 | 144 | 0.1662 | 97.7 | Crystals: 0.1662 M.L. of Aα = 20% of 147 gm |
| KR-148 | 31.19 | 40.16 | IPA | 0 | 0 to −10 | 158 | 27.00 | 44 | Cryst: 27.0, TEA: 2 ml |
| KR-149 | 2.5 | 10.4 | MeOH | 0 | 0 to −8 | 168 | 1.43 | 69 | Cryst: 1.43, 20% SS enriched solution |
| KR-150 | 10.0 | 8.0 | MeOH | 0 | 0 to −8 | 144 | 6.43 | 46.31 | Cryst: 6.43 gr, S.M. heated for 8 hrs |
| KR-151 | 5.4 | 10.8 | MeOH | 2 | 5 to −6 | 150 | 1.47 | 95 | Stirring, Aα = 20%, Cryst. Redissolved, restored as 151A |
| KR-152 | 7.2 | 8 | MeOH | 2 | 5 to −3 | 144 | 3.12 | 35 | Cryst. After 48 hrs + 2° C. (24 hrs). Redissolved contd. Cryst: 3.1 A = 20% |
| KR-153 | 10.38 | 10 | MeOH | 2 | 5 to −2 | 135 | 5.71 | 55.7 | Crystal appeared, redissolved and started as 153A, Aα = 20% |
| KR-154 | 2.53 | 8 | IPA | 2 | 5 to −10 | 330 | 1.78 | 57.5 | Cryst: 1.79 Aα = 20% |
| Kr-155 | 7.7 | 10 | MeOH | 2 | 5 to −6 | 170 | 4.40 | 60.46 | Cryst: 3.46, Aα = 20%, ML of 151A refluxed, added fresh 2.0 gr 1:1 |
| KR-156 | 2.57 | 8.6 | IPA | 0 | 5 to −4 | 164 | 1.35 | 52.5 | Aα = 20% |
| KR-157 | 1.99 | 8 | IPA | 0 | 2 to −4 | 96 | 1.08 | 45.9 | |
| KR-158 | 5.63 | 33 | Heptane Toluene | −8 | −8 | 150 | 1.55 | 55.2 | KR-153 A Cryst, M.L. Wt: 11.53 |
| KR-159 & 159A | 5.85 | 8 | MeOH | 2 | 5 to 0 | 168 | 1.8 | 52.7 | |
| KR-160 | 2.7 | 10 | MeOH | 2 | 5 to −3 | 142 | 1.67 | 70.25 | M.L. taken for 160. A expt. Aα = 20% |
| KR-160A | 1.1 | 4.4 | MeOH | −6 | −3 to −10 | 170 | 0.61 | 49.25 | Seed crystal dissolved, added fresh seed crystal; changed to −10° C. |
| KR-161 | 3.60 | 8 | MeOH | 2 | 5 to −4 | 140 | 1.07 | 96.90 | M.L. taken for 161A expt. |
| KR-161A | 2.53 | 9 | MeOH | −6 | −6 to −10 | 210 | 0.47 | 94.07 | ML of KR 160 |
| KR-162 | 2.0 | 8 | n-propanol | 2 | 5 to −8 | 220 | No crystals | — | Kept in the fridge. |
| KR-163 | 2.0 | 6 | Butanol | −2 | 0 to −10 | 260 | 1.5 | 45.59 | |

TABLE 1-continued

| Expt. No. | Wt. of dia-A (gms) | % solution (w/w) | Solvent system | Seeding (° C.) | Temp. profile (° C.) | Time (hrs) | Wt. of crystals (SS) (gms) | % Purity of crystals (SS) | Remarks |
|---|---|---|---|---|---|---|---|---|---|
| KR-164 | 2.02 | 10 | Butanol | 5 | 5 to −10 | 70 | 0.82 | 49.23 | Julabo problem. Kept n the fridge. |
| KR-165 | 5.03 | 15 | Butanol | 5 | 5 to −10 | 70 | 1.08 | 42.3 | Kept in fridge for 2 days |
| KR-166 | 9.368 | 30 | MeOH | −10 | −10 to −15 | 262 | 10 | 44.17 | Julabo problem |
| KR-167 | 2.01 | 10 | MeOH.BuOH | 0 | 5 to −10 | 260 | 0.6 | 48.52 | BuOH:MeOH is 1:1 |
| KR-168 | 2.01 | 11 | MeOH | 0 | 5 to −6 | 142 | 0.81 | 46.5 | 1% water |
| KR-169 | 11.53 | 35 | Heptane/TEA | −2 | 0 to −10 | 214 | 7.86 | 46.1 | Hep:TEA 55:45; ML deteriation observed |
| KR-170 | 10.02 | 33 | Heptane/TEA | −2 | 0 to −6 | 96 | 9.18 | 46.3 | HeP:TEA = 60:40 |
| KR-171 | 10.02 | 33 | Heptane/TEA | −6 | −6 to −10 | 121 | 4.74 | 48.2 | Hep:TEA = 1:1 |
| KR-172 | 10.10 | 36 | Heptane/TEA Toluene | 0 | 0 to −5 | 166 | 6.3 | 46.1 | Hep:T:TEA = 10:2:8 |
| KR-173 | 9.9 | 32 | TEA/Heptane | 0 | 0 to −5 | 166 | 7.03 | 45.59 | HeP:TEA = 5.2:15.4; |
| KR-174 | 9.99 | 13.19 | MeOH | 0 | +19 to −10 | 120 | 1.01 | 95.05 | |
| KR-175 | 5.02 | 13.63 | MeOH | 1 | 5 to −10 | 122 | 0.54 | 93.57 | Refluxed for 1 hr, filtered |
| KR-176 | 4.99 | 10.31 | MeOH | 0 | 3 to −15 | 125 | 0.54 | 92.56 | Refluxed, filtered |
| KR-177 | 10.03 | 10.15 | MeOH | 0 | 3 to −15 | 125 | 1.36 | 93.44 | Refluxed, filtered |
| KR-178 | 10.09 | 13 | MeOH | 0 | 5 to −10 | 53 | 2.70 | 95 | Refluxed for 1 hr |
| KR-179 | 9.98 | 13.26 | MeOH | 0 | 5 to −10 | 126 | 1.70 | 92.45 | Refluxed for 1 hr, filtered |
| KR-180 | 15.0 | 13 | MeOH | 0 | 5 to −10 | 126 | 2.42 | 94.8 | Refluxed for 1 hr, filtered |
| KR-181 | 36.33 | 13 | MeOH | 0 | 5 to −10 | 68 | 13.31 | 96.5 | Refluxed for 1 hr, filtered |
| KR-182 | 33.8 | 13 | MeOH | 0 | 5 to −10 | 97 | 4.8 | 99 | ML of 174-178 |
| KR-183 | 10.09 | 13.5 | MeOH | 0 | 5 to −10 | 45 | 1.6 | 49.3 | All old samples mixed |
| KR-184 | 10 | 13 | MeOH | 0 | 5 to −10 | 100 | 1.62 | 96.45 | All old samples mixed |
| KR-185 | 15.17 | 13 | MeOH | 0 | 5 to −10 | 110 | 2.76 | 98 | All old sample mixed |
| KR-186 | 100 | 13 | MeOH | 1 | 5 to −2 | 17 | 54.36 | 47.3 | Refluxed for 1 hr, filtered |
| KR-187 | 100 | 13 | MeOH | 0 | 5 to −2 | 90 | 68 | 47.01 | Refluxed for 1 hr, filtered |
| KR-188 | 54.45 | 13 | MeOH | 0 | 5 to −2 | 24 | 37.67 | 45.21 | Moisture in MeOH 1.294 |
| KR-189 | 50.10 | 13 | MeOH | −2 | 5 to −7 | 50 | 25.38 | | |
| KR-190 | 40.02 | 10 | MeOH | −2 | 5 to −6 | 44 | 32.77 | 44.55 | |
| KR-191 | 25 | 13 | MeOH | +5 | 10 to 3 | 24 | 19.22 | 41.58 | Moisture MeOH 0.278 |
| KR-192 | 10.04 | 13 | MeOH | −1 | 5 to −2 | 24 | 6.38 | 45.67 | MeOH distilled over Na KR-10, 138, 146 material |
| KR-193 | 10.06 | 14.36 | MeOH | — | 0 to −10 | 48 | 6.09 | 46.8 | No seed crystal added, crystals started at −1° C.; No stirring |
| KR-194 | 10.01 | 13 | MeOH | −1 | 5 to −10 | 48 | 5.36 | 44.7 | |
| KR-195 | 10.08 | 13.5 | IPA/Hexane | 1 | 5 to −10 | 142 | 6.43 | 44.9 | IPA:Hexane 45:55 |
| KR-196 | 10 | 13.6 | IPA | 3 | 5 to −10 | 142 | 7.71 | 45.6 | |
| KR-197 | 9.08 | 8.22 | IPA | — | 20 to 3 | 26 | 4.80 | 46.5 | No seed added |
| KR-198 | 87.78 | 13 | MeOH | −1 | 5 to −15 | 139 | 11.60 | 97 | ML of KR 181-185 mixed. Conc. |
| KR-199 | 40.15 | 25 | Heptane/TEA | −3 | 5 to −17 | 67 | 6.88 | 41.23 | |
| KR-200 | 42.83 | 13 | MeOH | — | 5 to −1 | 30 | 8.12 | 47.4 | No seed crystal |
| KR-201 | 40.06 | 13 | MeOH | 0 | 15 to 0 | 24 | 10.24 | 47.58 | No data |
| KR-202 | 20.09 | 13 | MeOH | 0 | 5 to 0 | 80 | — | — | 3.92 ACOH added at 2° C. |
| KR-203 | 18.7 | 13 | MeOH | 0 | 5 to −5 | 30 | 11.13 | 46.92 | 2.98 gr ACOH added |
| KR-204 | 17.69 | | MeOH | −2 | 5 to −4 | 98 | 7.84 | 44.5 | Methyl ester added (0.1 gr) |
| KR-205 | 17.68 | 13 | MeOH | 0 | 5 to −6 | 98 | 0.45 | 45.73 | Without methylester |
| KR-206 | 10.02 | 13.5 | MeOH | −2 | 4 to −7 | 42 | 5.63 | 45.23 | ML added 1.5 |
| KR-207 | 10.02 | 13.3 | MeOH | −2 | 5 to −7 | 42 | 6.6 | 44.77 | ML added 0.5 gr. |
| KR-208 | 13.3 | 13 | MeOH | −6 | 5 to −7 | 42 | 6.06 | 44.93 | ML added 0.5 gr |
| KR-209 | 10.01 | 13.8 | MeOH | −2 | 5 to −7 | 42 | 4.76 | 45.12 | Without ML addition |

TABLE 1-continued

| Expt. No. | Wt. of dia-A (gms) | % solution w/w | Solvent system | Seeding Temp. (° C.) | Temp. profile (° C.) | Time (hrs) | Wt. of crystals (gms) | % Purity of crystals (SS) | Remarks |
|---|---|---|---|---|---|---|---|---|---|
| KR-210 | 10 | 13 | MeOH | −1 | 2 to −10 | 76 | 7.49 | 46.89 | Less seed crystals 2-3 at −6. After 1 hr of seeding crystal growth formed. |
| KR-211 | 10.04 | 13 | MeOH | −1 | 22 to −10 | 76 | 7.2 | 45.91 | Less seed crystal. |
| KR-212 | 11.75 | 13 | MeOH | −1 | 23 to −9 | 76 | 5.63 | 43.71 | KR 206 to 208 MLs mixed |
| KR-213 | 65.70 | 30 | MeOH | −8 | 82 to −15 | 120 | 20.05 | 45.21 | ML of KR-198 gummy material |
| KR-214 | 10.04 | 10 | MeOH | 2 | 22 to −15 | 120 | No crystals | — | MLs of KR 186-194 mixed, conc. Iron cryst. Added (100 mg) |
| KR-214A | 10.4 | 10 | MeOH | −9 | 25 to −10 | 57 | 2.89 | 43.26 | ML of 214 |
| KR-215 | 10.07 g | 13 | MeOH | — | 20 to 5 | 24 | — | — | Melted at 90° and added Iron rust crystals dissolved at R.T. No seed crystal |
| KR-215A | 10.07 | 14 | MeOH | −9 | 21 to −10 | 54 | 0.29 | 43.64 | ML of KR-215 |
| KR-216 | 9.98 | 13.27 | MeOH | 4 | 20 to −2 | 24 | 4.23 | 43.27 | Charcoal added (400 mg) refluxed and filtered |
| KR-217 | 30 | 13.7 | MeOH | −4 | 11 to −2 | 68 | — | — | Turbidity at 0° C. filtered, crystals at RT dissolved |
| KR-217A | 30 | 13.9 | MeOH | −10 | −10 | 24 | 12.98 | 43.05 | ML of KR 217 |
| KR-218 | 10 | 14 | MeOH | −10 | −10 | 68 | 6.79 | 44.27 | ML of 215A |
| KR-219 | 30 | 13 | MeOH | 1 | 12 to −5 | 28 | 5.11 | 42.57 | Melted at 100° C. for 2 hrs |

| Expt. No. | Wt. of dia-A (gms) | % solution w/w | Solvent system | Seeding Temp. (° C.) | Temp. profile (° C.) | Time (hrs) | Wt. of crystals (gms) | % Purity of crystals (SS) | Remarks |
|---|---|---|---|---|---|---|---|---|---|
| KR-220 | 16.53 | 9 | MeOH | −5 | −3 to −9 | 26 | 1.34 | 70.32 | KR-217A ML |
| KR-221 | 15.05 | 13 | MeOH | 1 | 12 to −5 | 30 | 0.61 | 43.62 | Iron rust 100 mg solid dissolved at R.T. |
| KR-222 | 15.13 | 8 | MeOH | 0 | 5 to −5 | 90 | 2.04 | 98.76 | ML of KR-220, slurry addition |
| KR-223 | 24.89 | 12 | MeOH | 0° C. | 5 to 0 | 90 | 11.33 | 45.43 | Slurry addition |
| KR-224 | 650 mg | 19.8 | MeOH | −1 | 0 to −2 | 24 | — | — | Crystals were used as seed crystals for KR-222 and KR-223; crystallization of Aα |
| KR-225 | 13.09 | 13.0 | MeOH | −3.6 | −3 to −15 | 60 | — | 38.27 | ML of KR-222. ACOH added equilibrate at 100° for 1 hr. gummy material not weighed |
| KR-226 | 10.02 | 21.08 | Heptane/TEA | 4 | +21 to −4 | 168 | — | — | Heptane:TEA 1:1 crystals observed at Low temp. dissolved at R.T. |

| Expt. No. | Wt. of dia-A (gms) | % solution w/w | Solvent system | Seeding Temp. (° C.) | Temp. profile (° C.) | Time (hrs) | Wt. of crystals (gms) | % Purity of crystals (SS) | Remarks |
|---|---|---|---|---|---|---|---|---|---|
| KR-227 | 19.53 | 10 | MeOH | 5 | 5 | 115 | 2.85 | 34.5 | 0.5 gr ACOH added. Equilibrated at 65° C. for 1 hr |
| KR-228 | 15.57 | 13 | MeOH | −4 | 2 to −4 | 92 | 2.48 | 42.5 | ML's mixed conc. equilibrated for 1 hr |
| KR-229 | 16.0 | 9 | MeOH | −3 | 0 to −3 | 46 | 2.77 | 42.07 | ML of KR 237. 0.5 gr ACOH added |
| KR-230 | 10.08 | 13 | MeOH | 7 | 7 to 8 | 48 | — | — | Iron rust added. Crystals observed dissolved at R.T. (1) Solution equilibrated for 2 hr. at 65° C. |
| KR-231 | 13.0 | 12.5 | MeOH | — | — | — | — | — | Equilibrated at 120° C. for 6 hr. |
| KR-232 | 15.04 | 13.6 | MeOH | 10 | 10 to −13 | 185 | 2.78 | 96 | Solid equilibrated at 120° C. for 2 hrs. |
| KR-233 | 13 | 13 | MeOH | 10 | 10 to −8 | 150 | 2.13 | 94.7 | Equilibrated at 120° C. for 2 hrs. Iron rust added. |

TABLE 1-continued

| Expt. No. | Wt. of dia-A (gms) | % solution (w/w) | Solvent system | Temp. profile (° C.) | Seeding Temp. (° C.) | Wt. of crystals (SS) (gms) | % Purity of crystals (SS) | Time (hrs) | Remarks |
|---|---|---|---|---|---|---|---|---|---|
| KR-234 | 30 | 13 | MeOH | 5 | 5 to −2 | 4.6 | 11.21 | 43.36 | Equilibrated at 110° C. for 1½ hrs. |
| KR-235 | 60 | 13 | MeOH | 7 | 10 to 4 | 96 | 1.67 | 98.2 | Equilibrate 120° C., 2 hrs. |
| KR-236 | 30 | 10 | IPA | +2 to +3 | +3 | 12.1 | 42.68 | 22 | Mixed sample equilibrate at 120° for 2 hrs |
| KR-237 | 13 | 13 | MeOH | −15 | −15 | 0.73 | 94 | 48 | ML of 232 |
| KR-238 | 15.1 | 13 | IBA | 3 | 3 | 20.54 | 39.7 | 144 | — |
| KR-239 | 99 | 13 | MeOH | +10 to +4 | 9 | 50.5 | 52 | 96 | Equilibrated at 120° for 4 hrs |
| KR-240 | 10 | 13 | MeOH | 8 to 10 | 9 | 1.96 | 39 | 9 | Melt sample + PEA added |
| KR-241 | 9.9 | 13 | MeOH | +10 | 10 | <100 | 32.78 | 94 | 1 ml NH$_3$/MeOH |
| KR-242 | 10 | 13 | MeOH | +10 | 10 | .95 | 44 | 94 | Quinidine at 6° C. added |
| KR-243 | 10 | 12.8 | MeOH | +18 to +3 | 14 | 3.46 | 47.02 | 96 | ACOH added. 0.33 gr S.M melted |
| KR-244 | 99.5 | 13 | MeOH | 18 to −7 | 8 | 1.39 | 94 | 140 | Melt of RUN-I from Pilot plant expt. |
| KR-245 | 92.85 | 13 | MeOH | +6 to −12 | 7 | — | — | 122 | Run I material without melting. No crystals, conc. to 17% and std. As KR-248 |
| KR-246 | 21.2 g | 26 | MeOH | +20 to +12 | 15 | 1.65 | 57.4 | 24 | KR-239 material |
| KR-246A | 19.35 | 25 | MeOH | +12 | 12 | 14.23 | 45.30 | 24 | ML of KR-246 |
| KR247 | 93.6 | 19.8 | MeOH/Heptane | +6 to −13 | 5 | 9.54 | 97.5 | 188 | ML Conc to 19.8% 140 g Heptane added ML of KR-244 |
| KR-248 | 92.85 g | 22% | MeOH | +6 to −12 | 5 | 6.06 | 95.4 | 122 | Heptane 140 g added ML of KR-245 |
| KR-249 | 20.08 | 22% | HTM | +20 to −6 | 0 | 2.20 | 96.3 | 47 | KR-250; 251; 252 |
| KR-250 | 20.0 | — | — | — | — | — | — | — | Melting of 1:1 mat. at 120° C., 140° C., 160° C., 180° C., 200° C. for 2 hrs |
| KR-251 | 0.51 g | 9 | Heptane THF | +10 to −14 | −6 | No crystals | — | 96 | Kept in deep fridge; THF:Hep (10:90) |
| KR252 | 0.51 | 9 | Heptane THF | +10 to −14 | −6 | No crystals | — | — | Kept with deep freezer in THF:Hep (10:98) |
| KR-253 | 22.7 | 22 | MeOH Heptane Toluene | +14 to −2 | 0 | 20.25 | 44.3 | 138 | Crystals are gummy nature |
| KR-254 | 20 | 22.07 | HTM | +20 to −1 | 5 | — | — | 50 | Gummy solid, dissolved at R.T. |
| KR-255 | 29.94 | 23.07 | MeOH + Tol | +8 to −16 | 0 | 4.5 | 44.52 | 150 | MeOH:Toluene 80:20 KR-239 melted |
| KR-256 | 25 | 20.18 | Tol + IPA | +8 to −1 | −7 | No crystals | — | 150 | Seed crystal present. Toluene:IPA 33:67, No crystals |
| KR-257 | 20 | 11 | MeOH:Toluene | 23 to −7 | 3 | 7.76 | 43.29 | 70 | Crystal dissolved before −5° C.; present after −5° C. addn. 12.16 g KR added at −10° C. and expt. Contd. MeOH:Tol 63:3.7 |
| KR-258 | 20 | 11.83 | MeOH:Toluene | 23 to −6 | 9 | 8.19 | 43.7 | 70 | KR-239 melt, MeOH:tol 151:3.75 |
| KR-259 | 17.36 | 16.2 | MeOH:Toluene | +20 to +2 | 14 | 7.05 | 43.3 | 46 | MeOH:Toluene 87:3.2 |
| KR-260 | 20.00 | 11.5 | Toluene/MeOH | 15 to −6 | 9 | 90 | No crystals | 35.39 | S.M. melted at 120° C. for 3 hrs. NH$_3$/.MeOH added, 2 ml; Tol. 3% |
| KR-261 | 20.04 | 11.5 | Toluene/MeOH | 15 to −6 | 9 | 90 | 0.52 | 41.00 | Melted at 120° C. for 3 hrs; Tol 3%; Blank no ammonia |
| KR-262 | 20 | 11.5 | Toluene/MeOH | 15 to −6 | 9 | 90 | 6.7 | 42.27 | 1 ml MeOH/NH$_3$ added at −5° C.; Tol. 3% |

TABLE 1-continued

| Expt. No. | Wt. of dia-A (gms) | % solution (w/w) | Solvent system | Seeding Temp. (° C.) | Temp. profile (° C.) | Time (hrs) | Wt. of crystals (SS) (gms) | % Purity of crystals (SS) | Remarks |
|---|---|---|---|---|---|---|---|---|---|
| KR-263 | 9.09 | 15 | Heptane/THF | +10 to −14 | −12 | 142 | — | — | Added one drop of TEA at −14° C. Crystals appeared but dissolved while filtering |
| KR-264 | 20 | 12 | MeOH/Benzene | −6 to −9 | −6 | | 42 | 7.7 | 46.23 KR-260 melted; Benzene 2.5% |
| KR-265 | 19.96 | 12 | MeOH/Benzene | −6 | −6 to 9 | | 42 | 1.98 | 43.02 Benzene 10% |
| KR-266 | 20.08 | 12.5 | MeOH | −5 | −1 to −17 | | 118 | No crystals | — ML of KR 247, 3 ml NH$_3$/MeOH added |
| KR-267 | 150.06 | 12 | MeOH | 8 | 20 to 2 | | 94 | 15.65 | 98 S.M. melted |
| KR-268 | 20.12 | 15 | Heptane/THF | 2 | 16 to 2 | | 46 | 5.63 | 44.34 2% THF, at R T crystals liquid became |
| KR-267 | 150.06 | 12 | MeOH | 8 | 20 to 2 | | 94 | 15.65 | 98 S.M. melted |
| KR-268 | 20.12 | 15 | Heptane/THF | 2 | 16 to 2 | | 46 | 5.63 | 44.34 2% THF, at R T crystals became liquid |
| KR-269 | 19.96 | 15 | Heptane/THF | 2 | 15 to −2 | | 46 | 1.96 | 43.97 4% THF |
| KR-270 | 5.12 | 25 | Diglyme/Heptane | 0 | 0 | | 24 | — | — Melted sample used for expt. No crystals; Diglyme 10% |
| KR-271 | 20.41 | 13.5 | THF/Heptane | 8 | 15 to −4 | | 92 | 45.91 | 45.91 6% THF |
| KR-272 | 125.71 | 22 | MeOH | 7 | 13 to −3 | | 28 | — | 41.05 ML of KR-267 Crystals mixed with ML and kept again for crystallization (KR-273). |
| KR-273 | 125.7 | 22.42 | MeOH | 8 | +11 to −6 | | 50 | 20.16 | 95.01 I |
| KR-274 | 112.85 | 22.12 | MeOH | 8 | 11 to −4 | | 120 | 3.52 | 87.02 ML of KR-273-II |
| KR-275 | 50.06 | 34.9 | MeOH | 19 | 19 to 8 | | 65 | — | — No crystals, oily layer |
| KR-276 | 107.64 | 22.15 | MeOH | 8 | 20 to +3 | | 124 | 11.20 | 97.63 ML of 274 concentrated and equilibrated-III |

| Expt. No. | Wt. of dia-A (gms) | % solution (w/w) | Solvent system | Seeding Temp. (° C.) | Temp. Profile (° C.) | Time (hrs) | Wt. of crystals (SS) (gms) | % Purity of crystals (SS) | Remarks |
|---|---|---|---|---|---|---|---|---|---|
| KR-277 | 175.64 | 32.06 | MeOH | 7 | 20 to 5 | 30 | — | — | Julabo started heating. Reaction stopped. No crystals; solution conc. |
| KR-278 | 88.37 | 22.34 | MeOH | 8 | 18 to −15 | 240 | 5.0 | 95.13 | ML of KR-276-IV |
| KR-279 | 155.96 | 25.35 | MeOH | 4 | +20 to −19 | 260 | — | — | No crystals. ML of KR-277 |
| KR-280 | 82.05 | 29.88 | MeOH | 5 | 15 to −10 | 137 | 1.93 | 91.56 | ML of 278 equilibrated-V |
| KR-281 | 150.42 | 23 | MeOH | 10 | 16 to +4 | 74 | 18.57 | 96.64 | Fresh dil-A equilibrated |
| KR-282 | 130.87 | 21.73 | MeOH | 10 | 15 to +5 | 97 | 18.89 | 98.04 | Recycle-I KR-281 ML |
| KR-283 | 110.18 | 22.06 | MeOH | 10 | 20 to 0 | 192 | 10.97 | 95.3 | Recylce-II, KR-282 ML |
| KR-284 | 75.34 | 23.05 | MeOH | 0 | 0 to −16 | 98 | 0.64 | 91.6 | ML of KR-280, 5$^{th}$ cycle-VI |
| KR-285 | 97.8 | 22.06 | MeOH | 10 | 15 to −6 | 75 | 2.48 | 88.6 | ML of KR-283, recycle-III |
| KR-286 | 40.0 | 22.4 | MeOH | 9 | 20 to −5 | 76 | 8.36 | 91.52 | KF 0.122 added. Solids from carboy equilibrated |
| KR-287 | 40.02 | 33.13 | N,N-diethylaniline | 9 | 20 to −15 | 360 | — | — | No crystals. Heptane added in between (50 g) N, NDEA 33% |
| KR-288 | 31.15 | 25.3 | MeOH | 10 | 15 to −12 | 260 | No crystals | — | KF added 100 mg at 9° C. First time crystals formed. Dissolved while filtering. Restarted no crystals. |
| KR-289 | 40.02 | 26.32 | Heptane/Hexane, N,N-DEA | 6 | 10 to −10 | 98 | 2.54 | 81.35 | Hexane added at 3° C. run-III material; N,N-DEA 25% Heptane 58% |

| Expt. No. | Wt. of dia-A (gms) | % solution (w/w) | Solvent system | Seeding Temp. (° C.) | Temp. Profile (° C.) | Time (hrs) | Wt. of crystals (SS) (gms) | % Purity of crystals (SS) | Remarks |
|---|---|---|---|---|---|---|---|---|---|
| KR-290 | 48.88 | 27.3 | Heptane, Hexane, N,N-diethylaniline | 7 | 10 to −11 | 205 | 24.6 | 49.07 | Run-III material N,N-DEA 13.3%; Hep 64.5% |

TABLE 1-continued

| Expt. No. | Wt. of dia-A (gms) | % solution (w/w) | Solvent system | Seeding Temp. (° C.) | Temp. Profile (° C.) | Time (hrs) | Wt. of crystals (SS) (gms) | % Purity of crystals (SS) | Remarks |
|---|---|---|---|---|---|---|---|---|---|
| KR-291 | 94.4 | 25.15 | MeOH | 7 | 13 to −7 | 100 | 3.2 | 94.24 | ML of KR-285 |
| KR-292 | 88.46 | 24.62 | MeOH | 7 | 10 to −10 | 120 | 23.96 | 60.3 | Two layers formed, lower layer became semisolid. ML of KR-291 |
| KR-293 | 73.64 | 42.36 | MeOH | 7 | 10 to −10 | 120 | — | — | Solids melted after filtration. (1) ML of KR-284 |
| KR-294 | 45.5 | 36.6 | N,N,-DEA heptane, hexane | 7 | 10 to −11 | 116 | — | — | Solution became two layers, lower layer became little thick. Mixed with KR-287 material N,NDEA 15.3% Hep 62% |
| KR-295 | 132.6 | 26.11 | MeOH | 7 | 10 to −10 | 166 | 20.02 | 96.44 | SAF-29 material which was equilibrated |
| KR-296 | 109.22 | 26.88 | MeOH | 7 | 10 to −12 | 142 | — | — | After 70 hrs made 33% solution, after making 33% black gummy mass formed as lower layer. Concentrated; no crystals |
| KR-297 | 200.13 | 25.05 | MeOH | 7 | 11 to −5 | 42 | 70.5 | 48.73 | Gummy material in bottom layer pilot plant, RUN-I material |
| KR-298 | 148.05 | 23.95 | MeOH | 7 | 20 to −5 | 70 | 37.52 | 90.7 | Run - III material equilibrated |
| KR-299 | 105.38 | 21.08 | MeOH | 7 | 10 to −1 | 180 | — | — | No crystals. ML of KR-298 |
| KR-300 | 147.68 | 22.67 | MeOH | 7 | 11 to 5 | 78 | 26.69 | 94.48 | |
| KR-301 | 279.57 | 29.98 | MeOH | 15 | 20 to 5 | 102 | 49.44 | 95.67 | SAF-30 equilibrated material |
| KR-302 | 20.06 | 23.9 | IPA | 13 | 15 to 12 | 54 | 16.32 | 44.5 | Old material recovered in KR expts. |
| KR-303 | 115.31 | 24.26 | MeOH | 11 | 17 to 2 | 142 | 24.48 | 94.03 | ML of KR-300 equilibrated |
| KR-304 | 30.55 | 15.18 | EtOH | 7 | 22 to 2 | 48 | 10.8 | 46.2 | Two layers. Lower layer gummy old samples mixed equilibrated |
| KR-305 | 230.13 | 29.70 | MeOH | 13 | 16 to 0 | 118 | 64.3 | 65.23 | ML of KR-301 |
| KR-306 | 90.83 | 21.36 | MeOH | 9 | 12 to −2 | 170 | 10.81 | 93.52 | ML of KR-303, III cycle |
| KR-307 | 214.4 | 30.18 | MeOH | 14 | 26 to 13 | 138 | — | — | After 60 hrs full crystals fallen out. Dissolved and kept again for crystalisation. No crystals, conc. wt. 195.14 |
| KR-308 | 165.76 | 30.17 | MeOH | 12 | 23 to 3 | 174 | 14.03 | 89.79 | ML of KR-305, III cycle |
| KR-309 | 80.02 | 24.25 | MeOH | 12 | 25 to 9 | 167 | 17.35 | 60.6 | No crystals, gumy layer separated ML of KR-306, IV cycle |
| KR-310 | 136.91 | 30.36 | MeOH | 10 | 15 to −10 | 115 | 10.02 | 95.63 | ML of KR-308, IV cycle |
| KR-311 | 195.94 | 30.10 | MeOH | 21 | 22 to 9 | 142 | 192.2 | 45.68 | ML of KR-307, after 20 hrs. Full crystals dissolved. Kept again for crystallization |
| KR-312 | 57.6 | 25.12 | MeOH | 11 | 12 to −8 | 230 | 2.22 | 89.87 | ML of KR-309, V cycle |
| KR-313 | 993 | 29.8 | MeOH | 18 | 22 to 0 | 120 | 260.70 | 66.67 | Equilibrated fresh material |
| KR-314 | 733 | 30.02 | MeOH | 14 | 20 to 8 | 167 | 78.26 | 45.23 | ML of KR-313 |
| KR-315 | 16.4 | 27.38 | MeOH | 15 | 24 to 12 | 23 | 5.40 | 94.34 | Crystals of KR-313 dissolved in MeOH and kept for crystallization |
| KR-316 | 1456.23 | 35.09 | MeOH | 15 | 25 to 6 | 156 | 169.47 18.53 | 92.21 75.46 | All old samples mixed and taken for crystallization |
| KR-317 | 126.89 | 29.13 | MeOH | 8 | 20 to −10 | 144 | 3.94 | 93.9 | ML of KR-310, equilibrated |
| KR-318 | 1259 | 33 | MeOH | 11 | 15 to 0 | 145 | 122.73 | 93.09 | ML of KR-316, equilibrated |
| KR-319 | 1137 | 32.19 | MeOH | 10 | 15 to 4 | 186 | 115.93 | 88.4 | ML of KR-318, III cycle |
| KR-320 | 1433 | 37.39 | MeOH | 13 | 23 to 2 | 165 | 197.82 | 80.9 | ML of KR-319, IV cycle |
| KR-321 | 1235.18 | 35.40 | MeOH | 12 | 24 to 2 | 236 | 30.21 | 87.26 | ML of KR-320, V cycle |
| KR-322 | 48.8 | 25.30 | MeOH | 12 | 20 to 10 | 70 | 25.7 | 44.16 | |
| KR-323 | 48.8 | 25.0 | MeOH | 18 | 23 to 15 | 90 | 18.8 | 47.2 | Crystals of KR 322 and ML mixed and kept for crystallization. Slurry seed added. |
| KR-324 | 41.2 | 27.0 | MeOH | 14 | 18 to 11 | 192 | — | — | Solids dissolved at RT. Crystals of KR-323 equilibrated at 110° C. and used for reaction |

TABLE 1-continued

| Expt. No. | Wt. of dia-A (gms) | % solution (w/w) | Solvent system | Seeding Temp. (° C.) | Temp. Profile (° C.) | Time (hrs) | Wt. of crystals (SS) (gms) | % Purity of crystals (SS) | Remarks |
|---|---|---|---|---|---|---|---|---|---|
| KR-325 | 414 | 35.0 | Hexane/IPA | −8 | 15 to −10 | 144 | 10.0 | 44.26 | ML of KR-324 conc. and used |
| KR-326 | 22.88 | 30.31 | MeOH | 13 | 28 to 13 | 115 | 23.43 | 46.5 | 46.50 |
| KR-327 | 10.70 | 21.7 | MeOH | 18 | 20 to 15 | 60 | 4.07 | 46.69 | |
| KR-328 | 10.60 | 19.06 | MeOH | 19 | 27 to 18 | 47 | 3.70 | 46.90 | $H_3BO_3$: 0.56 gr dissolved after heating and filtered |
| KR-329 | 11.43 | 20.4 | MeOH | 18 | 21 to | 67 | 5.20 | 46.70 | $NaHSO_3$: 0.91 g dissolved after heating |
| KR-330 | 6.9 | 25.17 | MeOH | 19 | 22 to 19 | 22 | 2.07 | 46.05 | |
| KR-331 | 29.39 | 23.59 | MeOH | 23 | 25 to 20 | 90 | 19.63 | 45.72 | dia A-crystals from KR-326 to 330 expts) heated dissolved, filtration |
| KR-0332-I | 10.04 | 25 | MeOH | 19 | 25 to 19 | 48 | 4.4 | 46.88 | Acid: 0.52 gm PTC: 0.018 gm |
| KR-332-II | 10.03 | 24.46 | MeOH | 19 | 25 to 19 | 48 | 4.69 | 46.81 | ACOH: 1.0 ml PTC 0.021 gm |
| KR-333 | 10.26 | 25.48 | MeOH | 21 | 26 to 15 | 94 | 4.75 | 47.02 | PTC: 0.03 g ACOH: 4 ml |
| KR-334 | 10.439 | 28.59 | MeOH | 21 | 26 to 15 | 94 | 6.05 | 46.40 | Old sample mixed equilibrated |
| KR-335 | 35.95 | 21.76 | MeOH | 18 | 27 to 13 | 69 | 4.15 | 46.78 | Mixed samples ML 326, 330, 331, 332-I, II |
| KR-336 | 9.56 | 22.16 | MeOH | 17 | 20 to 14 | 95 | 7.16 | 44.65 | |
| KR-337 | 9.81 | 24.62 | MeOH | 15 | 22 to 9 | 47 | 6.58 | 44.59 | |
| KR-338 | 10.12 | 18.12 | MeOH | 15 | 22 to 9 | 41 | 4.86 | 44.86 | |
| KR-339 | 7.00 | 14.45 | MeOH | 17 | 25 to 14 | 60 | 2.8 | 44.7 | Mixed cryst. Of KR-331, 332, 333, 334 equilibrated IPA:MeOH (25:75) |
| KR-340 | 10.72 | 23.69 | MeOH | 18 | 28 to 15 | 29 | 2.71 | 46.2 | Dia-A pilot plant batch |
| KR-341 | 9.87 | 25.32 | MeOH/Acetone | 18 | 28 to 15 | 29 | — | — | 1% acetone added, No crystals |
| KR-342 | 37.65 | 22.46 | MeOH | 18 | 25 to 4 | 93 | 25.3 | 45.24 | Dia-A treated with NaOH and extracted with $CH_2Cl_2$ |
| KR-343 | 6.98 | 20.42 | MeOH | 15 | 25 to 5 | 215 | 0.5 | 89.44 | Flask broken while filtering solids SAF-31 material without equilibration |
| KR-344 | 23.11 | 25.4 | MeOH | 15 | 20 to 0 | 150 | — | — | SAF equilibrated material, no crystals SAF-31 |
| KR-345 | 20.20 | 25.63 | MeOH | 15 | 20 to 7 | 50 | 2.58 | 97.77 | SAF-34 material ACCl addn. no eq. |
| KR-346 | 20.10 | 25.76 | MeOH | 15 | 20 to 6 | 72 | 6.13 | 48.76 | SAF-35 material in toluene normal addn. no preferential |
| KR-347 | 38.42 | 33.45 | MeOH | 15 | 20 to 5 | 140 | 3.7 | 96.41 | ML of KR-345 + SAF-34 |
| KR-348 | 41.07 | 33.6 | MeOH | 15 | 20 to 8 | 100 | 5.79 | 94 | SAF-38 material |
| KR-349 | 45.43 | 32.96 | MeOH | 15 | 20 to 7 | 120 | 7.43 | 95 | SAF-39 material |
| KR-350 | 34.72 | 32.16 | MeOH | 15 | 20 to 2 | 135 | 3.90 | 96.56 | ML of KR-347 |
| KR-351 | 89.39 | 33.86 | MeOH | 15 | 20 to 10 | 100 | 20.45 | 48.22 | SAF 36 + 37 material (Toluene expts.) |
| KR-352 | 48.18 | 33.14 | MeOH | 15 | 18 to 4 | 126 | 7.16 | 96.80 | SAF-33 material |
| KR-353 | 38 | 31.57 | MeOH | 10 | 10 to 1 | 118 | 9.8 | 71.96 | Crystals are gummy material two layers in solution ML of KR-349 |
| KR-354 | 99.99 | 33.02 | MeOH | 12 | 20 to 10 | 94 | 13.62 | 96.27 | SAF-41 material, ACCl addition |
| KR-355 | 100 | 32.98 | MeOH | 15 | 20 to 4 | 96 | 21.89 | 80.40 | KR-354 ML |
| KR-356 | 106.79 | 32.35 | MeOH | 15 | 20 to −7 | 48 | — | — | KR-348, 350, 352 ML mixed. Two layers found at 70° C. dil. to 20% used for 356A expt. |
| KR-356-A | 106.79 | 19.8 | MeOH | 7 | 20 to −7 | 100 | 16.58 | 95.45 | KR-356 solution diluted ot 20% |
| KR-357 | 99.82 | 25 | MeOH | 6 | 20 to −2 | 98 | 15.79 | 95.44 | KR-355 ML, II cycle |
| KR-358 | 106.21 | 19.7 | MeOH | 6 | 20 to −6 | 95 | 12.16 | 96.70 | KR-356 ML I recycle; after addn. 0.37 g KF |
| KR-359 | 100.08 | 24.93 | MeOH | 3 | 26 to −2 | 118 | 14.15 | 97.15 | ML of KR-357, 3rd cycle |
| KR-360 | 110 | 19.9 | MeOH | 5 | 18 to −8 | 71 | 11.00 | 97.58 | ML of KR-358, II recycle |
| KR-361 | 100.33 | 25.006 | MeOH | 6 | 22 to −7 | 168 | 13.27 | 91.33 | ML of KR-359, 4th cycle |
| KR-362 | 113.82 | 19.99 | MeOH | 3 | 16 to −8 | 90 | 11.33 | 98.55 | ML of KR-360, III cycle |
| KR-363 | 116.53 | 20.078 | MeOH | 6 | 16 to −11 | 125 | 6.91 | 95.96 | ML of KR-362, IV cycle |
| KR-364 | 102 | 20.03 | MeOH | 6 | 16 to −8 | 100 | 10.34 | — | ML of KR-361, V cycle |
| KR-365 | 106.62 | 20.16 | MeOH | 5 | 15 to −9 | 116 | 11.22 | 95.54 | ML of KR-364, VI cycle |

TABLE 1-continued

| | | | | | | | | | |
|---|---|---|---|---|---|---|---|---|---|
| KR-366 | 129.32 | 21.30 | MeOH | 4 | 20 to −11 | 168 | 7.12 | 95.3 | -ML of KR-363 |
| KR-367 | 51.43 | 33.00 | MeOH | 15 | 20 to 8 | 50 | 11.24 | 95.3 | SAF-42 material, New catalyst |

| Expt. No. | Wt. of dia-A (gms) | % solution (w/w) | Solvent system | Seeding Temp. (° C.) | Temp. Profile (° C.) | Time (hrs) | Wt. of crystals (SS) | % Purity of crystals (SS) (gms) | Remarks |
|---|---|---|---|---|---|---|---|---|---|
| KR-367A | 51.45 | 32.68 | MeOH | 14 | 20-9 | 72 | 9.65 | 90.8 | ML of KR-367 |
| KR-368 | 107.21 | 20.60 | MeOH | 6 | 150 to −5 | 170 | 7.0 | 93.4 | KR-365 ML + SAF 43 (11.0 g) |

TABLE 2

ESTERS

| Expt. No. | Reaction conditions | Solvent | Catalyst | Mode of addition | Wt. of dia-A (gms) | Ratio of isomers (SR:SS) | Remarks |
|---|---|---|---|---|---|---|---|
| SAF-32 | Addn. at −5° C. for 90 min. and maintained RM @ −3 to +2 for 90 min. and +2 to +3 for 120 min. | DCE | TBAB | Normal addition | 43.01 g | 46.7:42.7 | *Normal addition is MPBA + ACCl to NaCN and PTC solution. This material is used for KR-352. ACCl = Acid chloride |
| SAF-33 | ACCl addition at −4° C. for 75 min. and maintained RM @ −1 to −4 for 150 min. | DCE | TBAB | ACCl addition dropwise to MPBAcyanohydrin | 48.182 g | 45.78:48.3 | — |
| SAF-34 | Addition of ACCl at −10° C. | DCE | TBAB | ACCl addition dropwise to MPBAcyanohydrin | 41.27 g | 45.5:45.22 | This material is used for KR-345 |
| SAF-35 | Addition of ACCl at 27° C. 60 minutes and maintained @ 27° C. for 300 min. | Toluene | TEBA | *Normal addition | 44.05 | 41.94:2.82 | This material is used for KR-346 |
| SAF-36 | Addition of ACCl at −5° C. for 80 minutes and maintained the reaction mixture at −3 to −5 for 2 hrs and left overnight | Toluene | TEBA | ACCl addition dropwise to MPBAcyanohydrin | 45.0 | 44.5:44.97 | — |
| SAF-37 | Addition of ACCl at 25° C. in 45 min. and maintained the RM @ 26° C.; for 300 minutes | Toluene | TEBA | ACCl addition dropwise to MPBAcyanohydrin | 45.0 | 41.5:42.72 | |
| SAF-38 | Addition of ACCl at 0° C. to +4 for 85 min. maintained the RM at 0 to −1 for 300 min. | DCE | N,N-dimethyl, N-butyl-α-phenyl-ethyl-ammonium-bromide | ACCl addition dropwise to MPBAcyanohydrin | 41.07 | 44.52:43.5 | This material is used for KR-348 |
| SAF-39 | Addition of ACCl at 0 to −1° C. for 60 min and RM maintained at 0 to −2 for 180 min | DCM | TBAB | ACCl addition dropwise to MPBAcyanohydrin | 45.43 | 43.94:41.14 | This material is used for KR-349 |
| SAF-40 | Addition of ACCl at 25° C. for 105 min and maintained RM at 25° C for 200 hrs | DCE | TBAB | ACCl addition dropwise to MPBAcyanohydrin | 6.82 | 42.5:41.5 | Material lost while conc. |
| SAF-41 | Addition of ACCl at −5 to −7° C. for 60 min. and maintained RM at −3 to −0° C. for 150 min. | DCE | TBAB | ACCl addition dropwise to MPBAcyanohydrin | 20.09 | 43:44 | This material is used for KR-354 |
| SAF-42 | Addition of ACCl at −3 to −2° C. for 85 min. and maintained RM at −3 to −1° C. for 135 min. | DCE | N,N-dimethyl, N-butyl-α-phenyl-ethyl-ammonium-bromide | ACCl addition dropwise to MPBAcyanohydrin | 37.00 g | 43.2:41.8 | This material is used for KR-367 |

We claim:

1. A process for preparation of (S)-α-cyano-3-phenoxybenzyl-(S)-2-(4-chlorophenyl) isovalerate (S,S isomer), said process comprising the steps of:
   a) crystallizing (RS)-α-cyano-3-phenoxybenzyl-(S)-2-(4-chlorophenyl) isovalerate (diastereomer-A), in the presence of crystals or a slurry of S,S isomer of a purity of 99% or greater in a solvent that is a saturated solution of 1,2-dichloroethane to obtain crystals of S,S isomer from mother liquor;
   b) epimerizing the mother liquor enriched with R,S isomers, and
   c) recycling the mother liquor for further crystallization.

2. The process as claimed in 1, wherein diastereomer-A is prepared by addition of (S)-(+)-2-(4-chlorophenyl)isovaleroyl chloride to an aqueous solution of (RS)-α-cyano-3-phenoxybenzylalcohol in a two phase system using a phase transfer catalyst to form a solution.

3. The process as claimed in claim 2, wherein the phase transfer catalyst is a quaternary ammonium salt selected from the group consisting tetrabutyl ammonium bromide (TBAB), tetrabutyl ammonium hydrogen sulphate (TBAHS), triethyl benzyl ammonium chloride (TEBA), benzyltributylammonium chloride, and N-butyl-N,N-dimethyl-α-(S)-phenylethylammonium bromide or a mixture thereof.

4. The process as claimed in claim 3, the phase transfer catalyst is tetrabutyl ammonium bromide.

5. The process as claimed in claim 2, wherein the (S)-(+)-2-(4-chlorophenyl)isovaleroyl chloride is added to the aqueous solution of (RS)-α-cyano-3-phenoxybenzylalcohol over a period of time ranging from 60-240 minutes.

6. The process as claimed in claim 5, wherein the (S)-(+)-2-(4-chlorophenyl)isovaleroyl chloride is added over a period of time ranging from 100-120 minutes.

7. The process as claimed in claim 2, wherein (S)-(+)-2-(4-chlorophenyl)isovaleroyl chloride is added to the aqueous solution of (RS)-α-cyano-3-phenoxybenzylalcohol at a temperature ranging from −8° C. to +50° C.

8. The process as claimed in claim 7 wherein the temperature ranges from −4° C. to −2° C.

9. The process as claimed in claim 2, wherein after addition of the (S)-(+)-2-(4-chlorophenyl)isovaleroyl chloride the solution is maintained for a period of 30-180 minutes.

10. The process as claimed in claim 9 wherein the solution is maintained for 60-120 minutes.

11. The process as claimed in claim 1, wherein the crystallization is monitored by HPLC analysis wherein samples are withdrawn at intervals of 60 to 120 minutes.

12. The process as claimed in claim 1, wherein the solution of diastereomer-A is concentrated from the solvent under reduced pressure from 80-60 mmHg.

13. The process according to claim 12 wherein the solvent recovered from concentration is recycled and used to prepare into additional diastereomer-A.

14. The process as claimed in claim 1, wherein the S,S isomer is crystallized from a saturated solution of diastereomer A by seeding with crystals or slurry of S,S isomer of a purity of 99% or greater optionally in the presence of a base catalyst.

15. The process as claimed in claim 1, wherein the concentration of diastereomer A in solution is in the range of 10-40% w/w.

16. The process as claimed in claim 1, wherein the concentration of diastereomer A in solution is in the range of 25-30% w/w.

17. The process as claimed in claim 1 wherein the process of crystallization is controlled by cooling the solution to a temperature for a time sufficient to increase the amount of S,R isomer in supernatant liquid.

18. The process as claimed in claim 17, wherein crystals of the S,S, isomer remain undissolved in the solution when the temperature is cooled from ambient temperature.

19. The process as claimed in claim 17,wherein crystallization of the S,S isomer is conspicuous.

20. The process as claimed in claim 17, wherein the S,S isomer crystallizes when the temperature is decreased.

21. The process as claimed in claim 20, wherein only the S,S isomer crystallizes.

22. The process as claimed in claim 17, wherein the temperature of solution is monitored by analyzing samples of supernatant liquid by HPLC analysis at intervals of time ranging from 4-8 hrs.

23. The process as claimed in claim 22, wherein the process of crystallization is terminated when concentration of the S,R isomer in the supernatant liquid is in the range of 55-60% w/w.

24. The process as claimed in claim 1, wherein the crystals obtained are separated by centriftigation, decantation or filtration.

25. The process as claimed in claim 24, wherein the crystals are separated by filtration.

26. The process as claimed in claim 1, wherein crystallization is increased by stirring the solution.

27. The process as claimed in claim 1, wherein crystallization is increased by shaking the solution.

28. The process as claimed in claim 1, wherein the process of crystallization is carried out at a temperature in the range of −18° C. to 10° C.

29. The process as claimed in claim 1, wherein crystallization occurs in from 24 to 48 hours.

30. The process as claimed in claim 29 wherein crystallization occurs in from 30 to 72 hours.

31. The process as claimed in claim 1, wherein after removing SS isomer crystals, the mother liquor containing the S,R isomer is equilibrated either by concentration and heating; or with a base to obtain 1:1 ratio of SS:SR isomer and subjected to further crystallization.

32. The process as claimed in claim 31, wherein the process of crystallization is continued by addition of diastereomer-A in each cycle iteratively until crystals of S,S isomer are obtained.

33. The process as claimed in claim 31, wherein the mother liquor is equilibrated with an either inorganic or organic base.

34. The process as claimed in claim 31, wherein the mother liquor is equilibrated by selecting a base that does not catalyze the formation of side products from diastereomer-A.

35. The process as claimed in claim 31, wherein the base is selected from the group consisting of earth metal hydroxides, earth metal carbonates, nitrogen containing bases, organic bases, quaternary ammonium salts, halides of alkali metals and ammonium halides or a mixture thereof.

36. The process as claimed in claim 31 wherein the base is selected from the group consisting of sodium hydroxide, potassium hydroxide, sodium carbonate, ammonia, dimethylamine, trimethylamine, triethylamine, N,N-dimethylaniline, tetrabutylammonium bromide, triethylbenzyl ammonium chloride, triethylbenzylammonium bromide, benzyl tributyl ammonium chloride, and N-butyl-N,N-dimethyl-$\alpha$-(S)-phenyl ethylamine or a mixture thereof.

37. The process as claimed in claim 30, wherein the base selected for equilibration of the mother liquor is potassium fluoride.

38. The process as claimed in claim 37, wherein the potassium fluoride used ranges from 2-10 mole percent.

39. The process as claimed in claim 38, wherein the potassium fluoride used ranges from 4-6 mole percent.

\* \* \* \* \*